United States Patent
Tomas et al.

(10) Patent No.: US 9,060,477 B2
(45) Date of Patent: Jun. 23, 2015

(54) GENETIC LOCI ON MAIZE CHROMOSOMES 3 AND 4 THAT ARE ASSOCIATED WITH FUSARIUM EAR MOLD RESISTANCE

(75) Inventors: Adriana Tomas, Newark, DE (US); Stanley Luck, Wilmington, DE (US); Jamie Anne Layton, Newark, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 970 days.

(21) Appl. No.: 13/005,855

(22) Filed: Jan. 13, 2011

(65) Prior Publication Data

US 2011/0185457 A1 Jul. 28, 2011

Related U.S. Application Data

(60) Provisional application No. 61/298,233, filed on Jan. 26, 2010.

(51) Int. Cl.
| | | |
|---|---|---|
| *A01H 1/04* | (2006.01) | |
| *A01H 1/02* | (2006.01) | |
| *A01H 5/10* | (2006.01) | |
| *A01H 1/00* | (2006.01) | |
| *C12Q 1/68* | (2006.01) | |

(52) U.S. Cl.
CPC .. *A01H 5/10* (2013.01); *A01H 1/00* (2013.01); *A01H 1/04* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

FOREIGN PATENT DOCUMENTS

| WO | 2008/087208 A2 | 7/2008 |
|---|---|---|
| WO | 2010/120727 A1 | 10/2010 |

OTHER PUBLICATIONS

Ding et al. (Mol. Breeding (2008) 22: pp. 395-403).*
PHM12969 marker location PDF from MaizeGDB accessed Feb. 24, 2014.*
PHM18211 marker location PDF from MaizeGDB accessed Feb. 24, 2014.*
bnlg1012 marker location PDF from MaizeGDB accessed Feb. 24, 2014.*
U.S. Appl. No. 61/298,233, filed Jan. 26, 2010.
Ali et al., Molecular Mapping of QTLs for Resistance to Gibberella Ear Rot, in corn, Caused by *Fusarium graminearum*, Genome, 2005, 521-533, 48, NRC Canada.
Ding et al., QTL Mapping of Resistance to *Fusarium* Ear Rot Using a RIL Population in Maize, Molecular Breeding, 2008, 395-403, 22, Springer.
Duvick et al., Prospects for Reducing Fumonisin Contamination of Maize through Genetic Modification, Environmental Health Perspectives, 2001, 337-342, 109(2).
Perez-Brito et al., QTL Mapping of *Fusarium moniliforme* Ear Rot Resistance in Highland Maize, Mexico, Agrociencia, 2001, 181-196, 35.
Robertson-Hoyt et al., QTL Mapping of *Fusarium* Ear Rot and Rumonisin Contamination Resistance in Two Maize Populations, Crop Science, 2006, 1734-1743, 46.
Robertson-Hoyt et al., Relationships among Resistances to *Fusarium* and *Aspergillus* Ear Rot and Contamination by Fumonisin and Aflatoxin Maize, Phytopathology, 2007, 311-317, 97(3).
Zhang et al., QTL Mapping of *Fusarium moniliforme* Ear Rot Resistance in Maize. 1. Map construction with Microsatellite and AFLP Markers, Journal of Applied Genetics, 2006, 9-15, 47(1).
Nathan J. Van Opdorp, Predicted QTL locations for *Fusarium* ear rot (FER) resistance in maize and the generation of improved FER resistant maize inbred, PHD Thesis Dissertation, Purdue University, West Lafayette, Indiana, 2009, pp. 1-44.
Miedaner, Thomas et al., Genetic variation for resistance and mycotoxin content of European maize inoculated with Fusariumgraminearum and F-verticillioides, Cereal Research Communication, 2008, vol. 36, No. Suppl. B, pp. 45-58.
Eller, Magen S. et al., Selection for Reduced *Fusarium* Ear Rot and Fumonisin Content in Advanced Backcross Maize lines and Their Topcross Hybrids, Crop Science, Sep. 27, 2010, vol. 50, No. 6, pp. 2249-2260.
PHM-12969 marker location PDF from MaizeGDB accessed Feb. 24, 2014.
PHM 18211 marker location PDF from MaizeGDB accessed Feb. 24, 2014.
Bnig 1012 marker location PDF from MaizeGDB accessed Feb. 24, 2014.
M. Liakat et al., Molecular mapping of QTLs for resistance to *Gibberega* ear rot, in corn, caused by *Fusarium grarninearum*, Genome, 2005, vol. 48, pp. 521-533.
BB1664 International Search Report—PCT/US11/22489, 2012.
M. Enrico PE. et al., Mapping quantitative trait loci (QTLs) for resistance to *Gibberella zeae* infection in maize, Mol Gen Genet, 1993, pp. 11-16, vol. 241.
EP Search Report EP 14 18 9434.

* cited by examiner

*Primary Examiner* — David T Fox
*Assistant Examiner* — Jared Shapiro

(57) ABSTRACT

The invention relates to methods and compositions for identifying and selecting maize plants with enhanced resistance to *Fusarium* ear mold. Maize plants generated by the methods of the invention are also a feature of the invention.

2 Claims, 6 Drawing Sheets

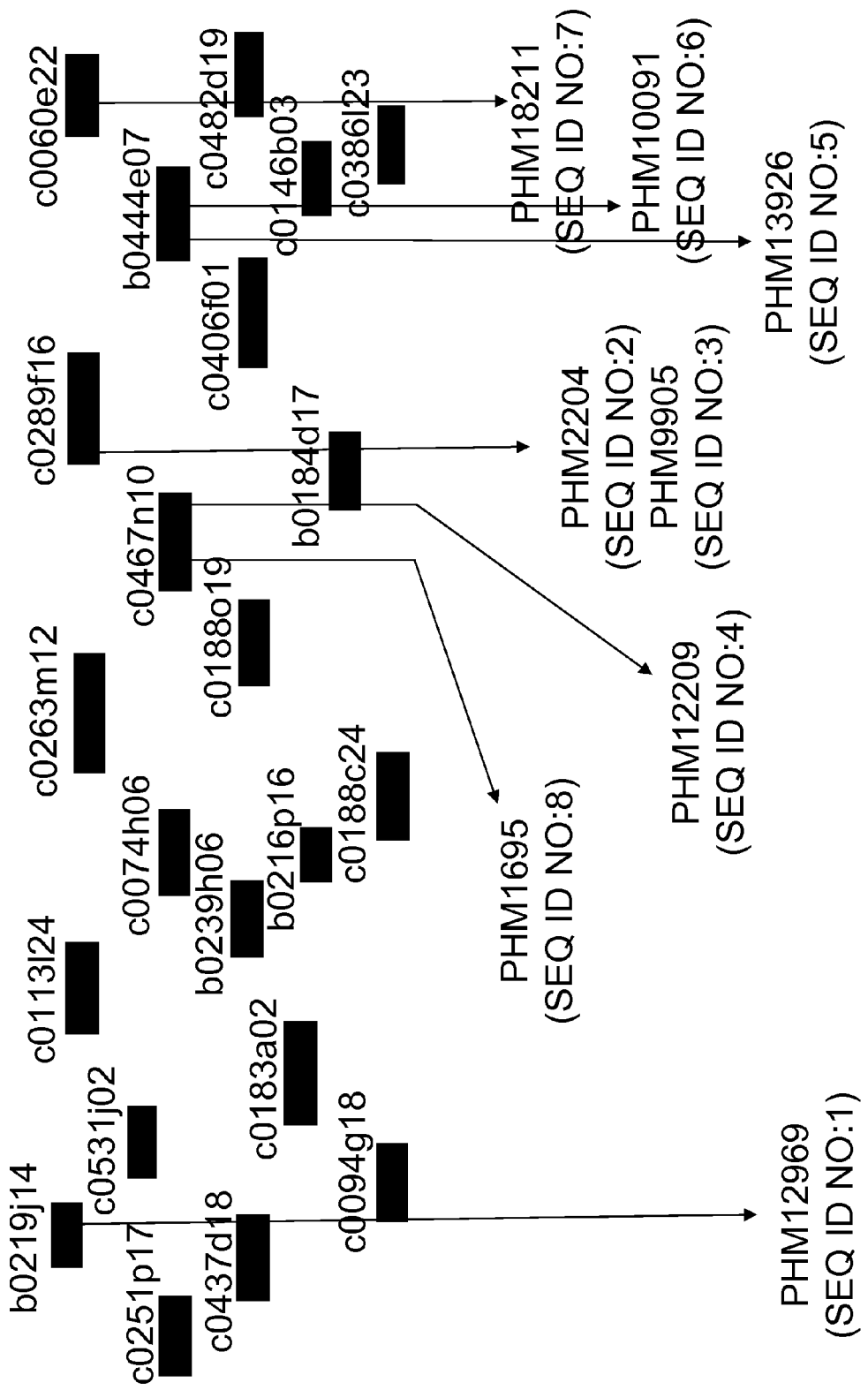
FIG. 1 Chromosome 3 QTL Location

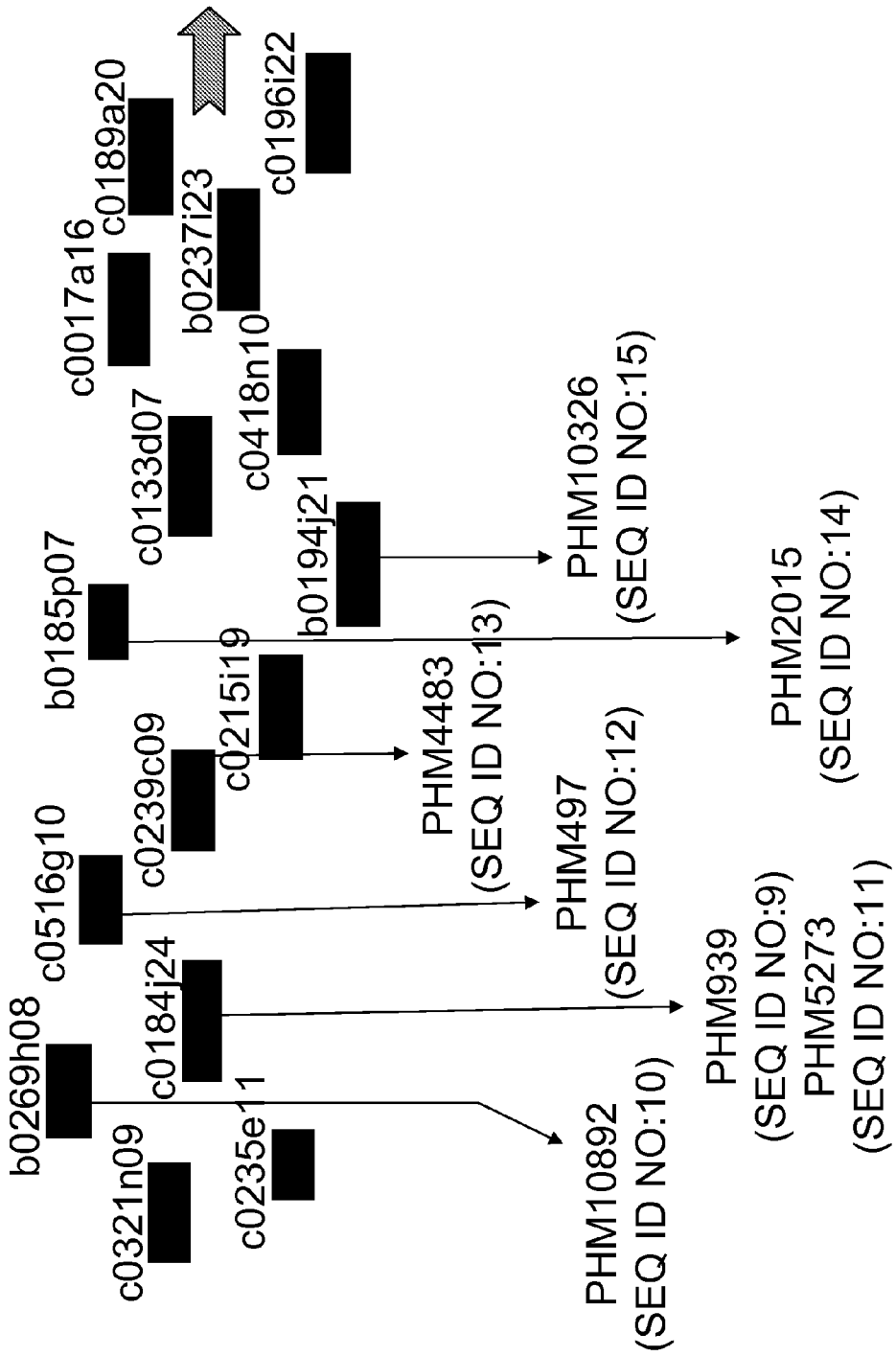

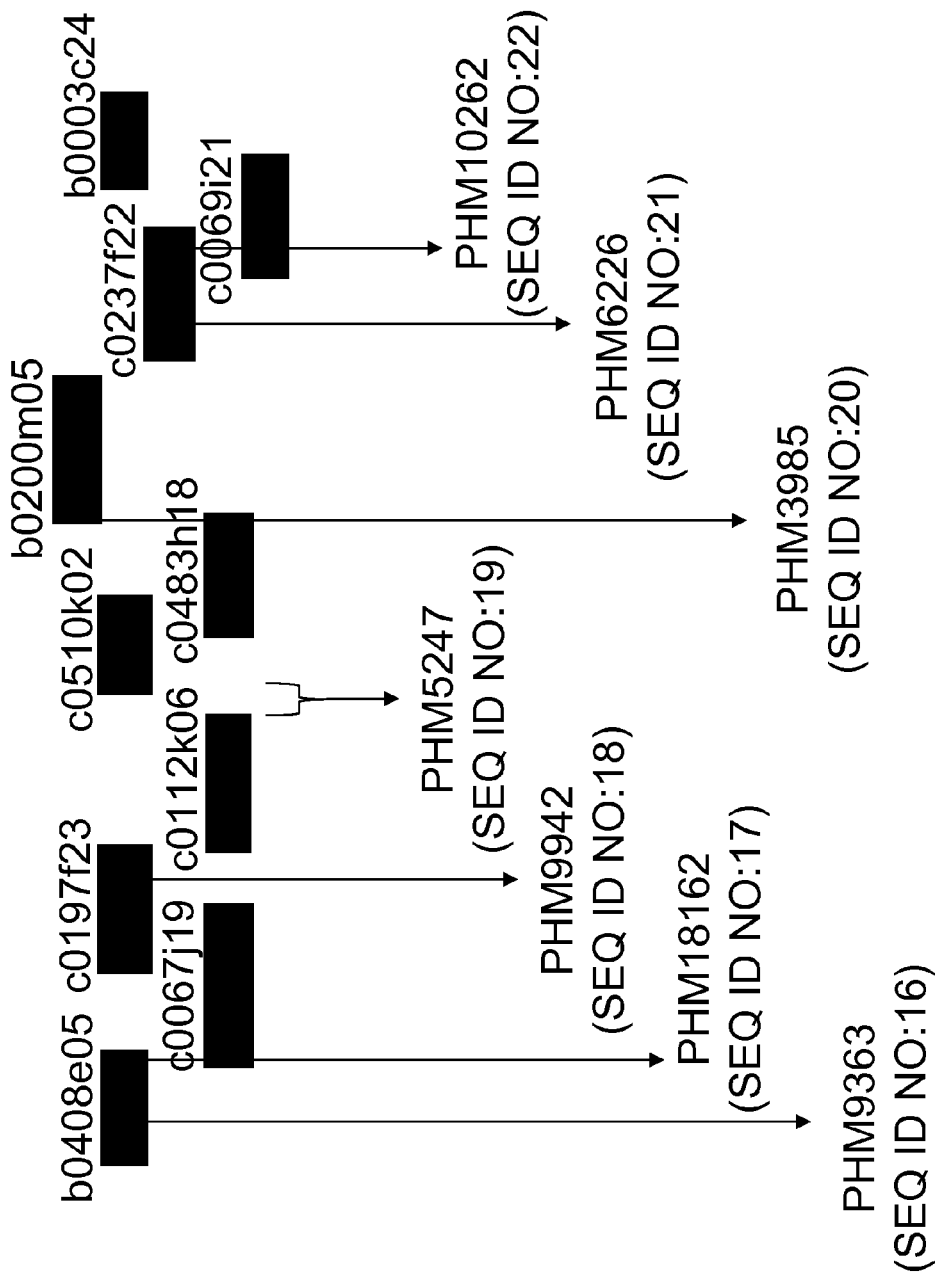
FIG. 2B Chromosome 4 QTL Location

FIG. 3: Associations between marker loci on chromosome 3 and Fusarium ear mold resistance in a stiff stalk subpopulation Boxed region indicates marker loci that are significantly associated with Fusarium ear mold resistance at $p \leq 0.001$.

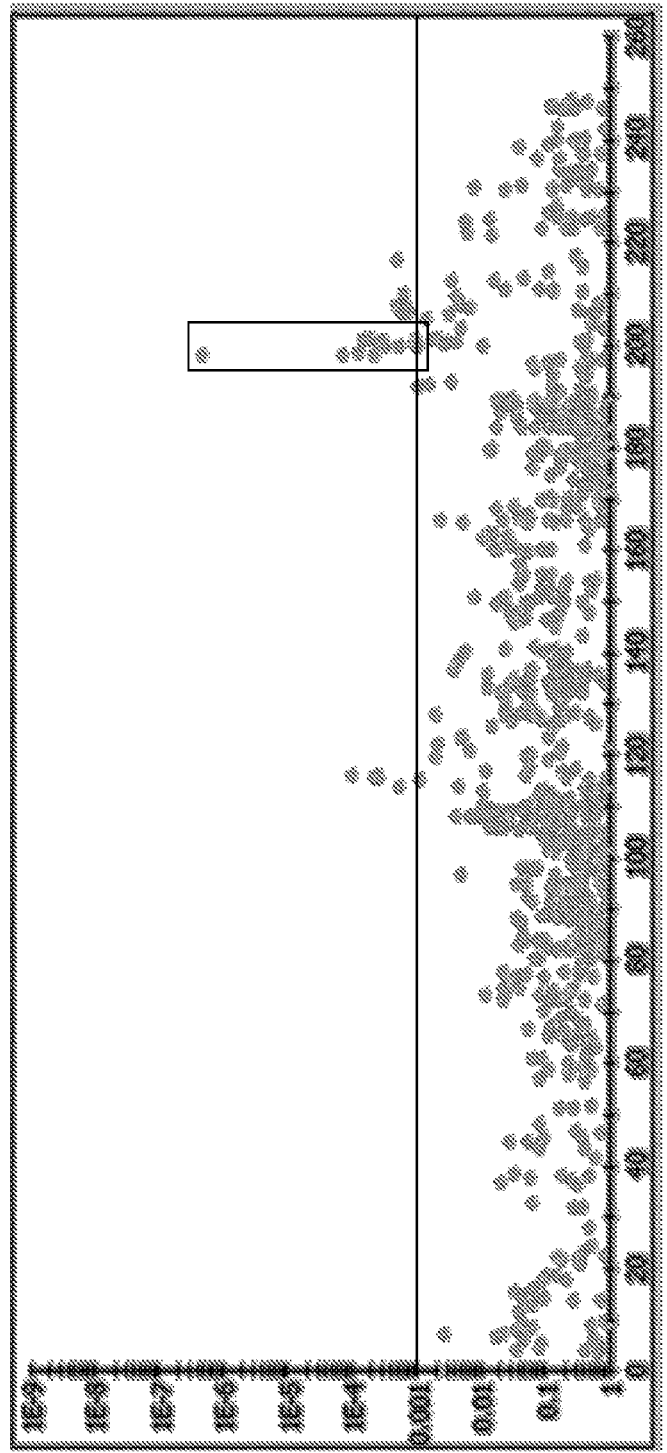
FIG. 4: Associations between marker loci on chromosome 4 and *Fusarium* ear mold resistance in a stiff stalk subpopulation
Boxed region indicates marker loci that are significantly associated with *Fusarium* ear mold resistance at $p \leq 0.001$.

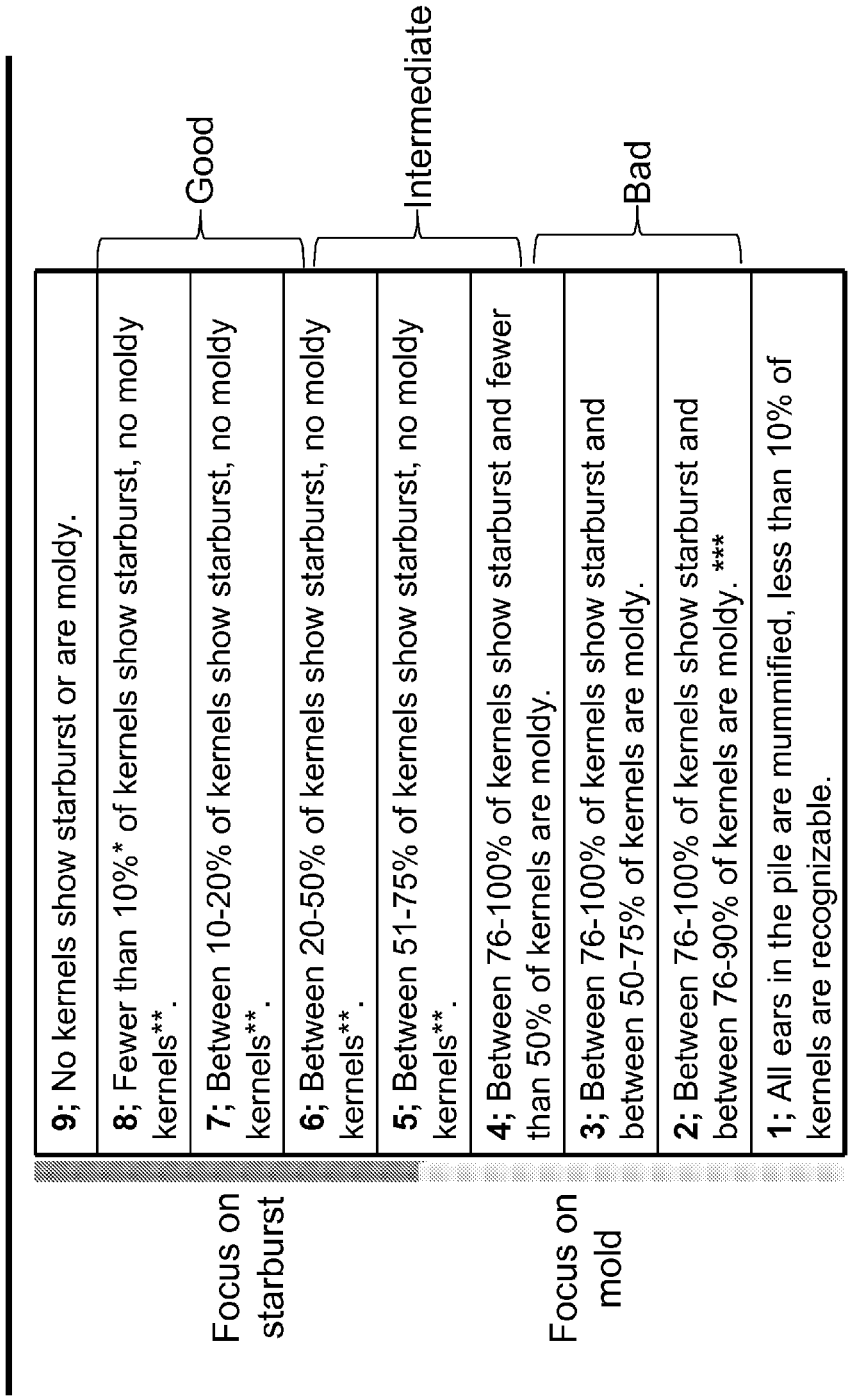

SEQUENCE LISTING

<160> NUMBER OF SEQ ID NOS: 126

<210> SEQ ID NO 1
<211> LENGTH: 490
<212> TYPE: DNA
<213> ORGANISM: artificial
<220> FEATURE:
<223> OTHER INFORMATION: PHM12969 reference sequence

<400> SEQUENCE: 1

| | |
|---|---|
| cggcacaccc cacttgcact ggacagggta cgggctcgcc gccgggatcg tgaccaagag | 60 |
| cctggacgtc gccaaccggg tgtcccggtc ggtgcgcgcc ggcaccgtgt gggtgaactg | 120 |
| ctacttcgcc ttcgacccgg acgcgccctt cggcgggtac aagatgagcg gcttcggccg | 180 |
| ggaccagggg ctggcagcca tggacaagta cctgcaggtc aagagcgtca tcaccgcgct | 240 |
| cccggactcg ccatggtatt gagttgagcc agggaccgac cgatggaacc ccatcgatct | 300 |
| cttcttgtgc agtgtacatg cgtcatgcgt gcgtgctcac acagctgggt tgctgctttg | 360 |
| tgcttgtgtt cgtctctggt ttgtggctca tgtgttagtc tgcaccctat ccttctgtac | 420 |
| gtagctgccg gacatgcata tagtatgtta agtacaccat ataaactcat ggtcatagct | 480 |
| ggccctgccc | 490 |

<210> SEQ ID NO 2
<211> LENGTH: 553
<212> TYPE: DNA
<213> ORGANISM: artificial
<220> FEATURE:
<223> OTHER INFORMATION: PHM2204 reference sequence

<400> SEQUENCE: 2

| | |
|---|---|
| gattatgaga aaaatcccag tcacgacgag ttcttgtatt atggaatccc agtcacaacg | 60 |
| agttcttgta ttatggagag gtttgcttat gatggggtca agaatggcca tgggaacatg | 120 |
| attcattcag atgcggacct tttctttttt gataagcaga gtggtaggga gtttatggac | 180 |
| accaaaggca gtgaggatga agctgtggag gagatgagaa ctgcaggtaa tgcttttatg | 240 |
| gctgctgccc agtcaatgaa gggggtgact gacggcatga ggaagaggaa gagctgcgga | 300 |
| tatgaagatg cagcagctgt gaagtttgtg aagtacaagg ttgaagacag ctcgctgaag | 360 |
| gactacctgt cagcagctaa tggcataagc agtggcagtg aggtagagaa cccgcagtct | 420 |
| gatgatgaga tggaagaatc aaactgatgc atagaaacga gatcaccgc taatgcttac | 480 |
| tttggacagt tgcttttgag agttccttga cagccgcctt ttttgagcca gaccatttct | 540 |
| ttattttatt tta | 553 |

<210> SEQ ID NO 3
<211> LENGTH: 651
<212> TYPE: DNA
<213> ORGANISM: artificial
<220> FEATURE:
<223> OTHER INFORMATION: PHM9905 reference sequence

<400> SEQUENCE: 3

| | |
|---|---|
| gaagtttccg aaatcgtcac caatccggcg agcgtcgacg cggacggcag gctcaggatt | 60 |
| tcgccgttcc acgaccccgc gtccgcgccg cacggttgca gcctttgccc tgacaacatg | 120 |
| tgcaaggtac cacgattatt acaacagcat attgtatttt aagatgtctg gatgcccata | 180 |
| ctctactttc gacactgatg aaatctctgt gcaatgcaca tagtcaacag tcatgtcgag | 240 |
| atgcggaaac tcaccggtaa ttcagcaata aaccaaagat gtgctcttac cacgtgcagt | 300 |

```
gcagggcaag atactgggga ggatccaggc aacaggcagt gacaagaagc ggcgcttcat      360
ctacatcggt gacgggaagg gagattactg cccgtccctc aagctggggg aaggggacca      420
cgtcatggca agggagaact accccctgtg gcatctcatc tgcgacaaca agcagcttct      480
caaggctgag gttcatccat ggaacagcgg cgaggaactg aaaagacgc tgcttaagtt       540 ggccggcggc ggcgaagtga tcagtccacc tgcacaagct cccagtttg actacagcaa       600 atgcgagatg agcaatccag catcctgccc tccgtcgact ttccgttaat a               651

<210> SEQ ID NO 4
<211> LENGTH: 473
<212> TYPE: DNA
<213> ORGANISM: artificial
<220> FEATURE:
<223> OTHER INFORMATION: PHM12209 reference sequence

<400> SEQUENCE: 4
cggcggcgcc cccaattat tgatggtctt tgtgccaatg aatagcacat attttgctg         60 gaacaaacct gatccatgtg ttactcaaaa ctgcagttat gtgatttata tgaaaatgac      120 tcaatttcg acaaatttga gtgttgtcaa agtggtgatg gattaagagt agcaactggt       180
tcctacaggt agtctcatat gctcgtccag ttgtaataca gcttggctcc attaacagga      240
actaactagc tgtttgtgat cttcagcaac attttttcgcg tgtttggttg ccgttctggt     300
agcagtgaag caacaacact tgaagcaacc cgaaacccta caaggtaatg ctactttttca    360 aagaaaatgt ttgaagcaaa actattcaac ttctaagcat gttattgttt cttcatgtaa      420
attgatttcc atacaccaag ctgttaatgg tcatagctgt ccctttcccc cct             473

<210> SEQ ID NO 5
<211> LENGTH: 515
<212> TYPE: DNA
<213> ORGANISM: artificial
<220> FEATURE:
<223> OTHER INFORMATION: PHM13926 reference sequence

<400> SEQUENCE: 5
gccacagaca ttattcctaa attttctgta tgtaacaatc aataatctgg tcaacaggtg       60
ccgatttgcg agaacagtgc gagcatctcc gatccgctga gcagcgaagg ggcctcaacc      120
tctctgtcgc tgaacgtgcc acgccacggc gtcacctccg tctccgagag gcggccttg       180 gacctgaatt cgacggagga agacgacagc agggcggacg cgtcgtcggc atcggcatca     240
ggtgcaggga ccagaccacc gttcccggca gcgcagacgg agccgctgct gcagccttcg      300
tcgcttggcc atgggcgcgg tcaccactgc tctcctttgg acctggagct ggccatgtcg      360
ctgcctgccc catccatcgg aacatgacgc gccgccgccg ccgtacttat cgccatggaa     420
tcccacgcag gtcgcgccak aattcgtcag cgcaggttgc caaggccgag gccgtgcgtg     480
cctgctgtct atggtcatag ctgtctgttc cccgg                                  515

<210> SEQ ID NO 6
<211> LENGTH: 667
<212> TYPE: DNA
<213> ORGANISM: artificial
<220> FEATURE:
<223> OTHER INFORMATION: PHM10091 reference sequence

<400> SEQUENCE: 6
tttcatccgt actaactttt ttttggcagt tgaaactcga gggtatacat gtggatgaag       60
```

```
aaaagactat caatgatcca gaacttctta tggaggtaat ttcattcatc ttggaaattg      120
gaatacacgt gctggcatgc agtaaatata accatccttc tcatttcatg tatcttttga      180
taactgtgaa taacattgca acaattggaa gtttggaaca cacattcaat gtgttaaaca      240
tcctatgtaa agtacattaa aatgaatgaa ctctgaattg agatgaatac aacaacacaa      300
acggtttatt tatgtacatc ttattccatt aacttacacg aaatgaagat gacaatgttc      360
tccataaatc aataacaaat cgcttgcaga tgatggagat acgggaagct gtcagtgatg      420
ccagtgattc tcaaaccctg gagaagatcc aatctcaggt tctgatctct gaataaagct      480
acacgtgcca taacataacc agggagcatg attgcgtcgc aatggtttct ggtctcatag      540 cctttttgttc ccttttccag attaaggcaa agctcgaaac ctggtccgat tccttccagg      600
aggcatttga caggaaggat tttgaccgtg cagtgaagcc acacagagga tggaattgcg      660
gggaaaa                                                                667

<210> SEQ ID NO 7
<211> LENGTH: 795
<212> TYPE: DNA
<213> ORGANISM: artificial
<220> FEATURE:
<223> OTHER INFORMATION: PHM18211 reference sequence

<400> SEQUENCE: 7
cgttgaaaaa cagaagaaag acgaccagga gaacttcgag gtaaagcagc tcggcgattt       60
aattgccggc ctgtttgcct atttcgaatg atatatatgc tgatgttatt tatgtgtgct      120
gtgatggttt cagggattcc acgacttcgt gcaggagatg gtctcgctca tggccagaga      180
ggtaactatc agcagctagc tagctagcta cctcatgttc atgccaatca aggtgcaaaa      240
tgtcgtgcgc tgcttcagca atcgatgatt aattaataat ctcgcgcgca ggagcccgtg      300
tacagcttgg ccgagctgca atccatgctg acgggatga tcaaggattt caccgcgcca      360
cagccttggc ctagcggctt cttctacact ggtggcggtg gcgtggcgg tggggcgtcg      420 tcgccgtcgc cgctcggcaa accaagcagc caagagcaga gtacggcttc gtcacgcttg      480
catccctacg ggttcgggga cgcgccgtgc ttcagccgca cggcgttctc acaatgatgg      540
cgatgatgaa taaataaatt gatacatgga tcgagctttt atgattttat ccttctggtt      600
ctggcagcaa tggggttttt ctcgctcgtg ctcgtggagg tggagggaga gtaggagcaa      660
cccgtgaccg tgaaagccat tgtccgccag ggtcaggctc tgatttgcag ttgcaattgc      720
tttggactgc ggctgcaggg atgaaagaag gtgaggtgga agataaccag gaaatgggaa      780
aaaaatttta aaaaa                                                       795

<210> SEQ ID NO 8
<211> LENGTH: 574
<212> TYPE: DNA
<213> ORGANISM: artificial
<220> FEATURE:
<223> OTHER INFORMATION: PHM1695 reference sequence

<400> SEQUENCE: 8
tcaaaagtcc taatccgggg tccgcgacgc gttccgggcc gccgcggcgg ggggctccg       60 gctttccccc ggcgggttct cgctgttcga cacgtgctac gacctgggcg gcgcagggt      120 ggtgaaggtg ccgaccgtgt cgatgcactt cgcggcggc gccgaggccg cactgccccc      180
cgagaactac ctcatccccg tggactccag gggcaccttc tgcttcgcgt cgcgggcac      240 cgacggcggc gtgtccatca tcggcaacat ccagcagcag gggttccgcg tggtgttcga      300
```

-continued

```
cggcgacggc cagcgcgtgg ggttcgcgcc caaaggctgc tgagagcccc caggccggag    360
tggtgaaccc gtccctctct cgagcgagga gagagagaga gagaacgcgc gcggcccttg    420
tggcgcagtt aattaattag cgagtgatta gctggtaatc aagtgagccg ccttgttagt    480
cataattaat ggatgcggtg gcttgtggtt gtgggtttgc tttgcttggc cttggatgct    540
gtgctgttaa aaaaaaccgc ggcactggca tttc                                574
```

<210> SEQ ID NO 9
<211> LENGTH: 477
<212> TYPE: DNA
<213> ORGANISM: artificial
<220> FEATURE:
<223> OTHER INFORMATION: PHM939 reference sequence

<400> SEQUENCE: 9

```
aaaatgaggg actggttcag aagtatggta aaagatcatc tgttcaagcc ccacgtactg     60
ggatgacgat gacgatgaca taccagagtg aacccagc cagacgatta agcagccgcc     120
gccactgcct cacgcccac agcaacagcc gttgcctcca cctcccgtcc agcagatgga    180
cgcctaccag cagcagtacc acatcacaag tgcagtgcag cctcaggttc cgtcgcatc     240 gctgccccat gcctacctcc agatccagca gcctgggcag gcatggcagc agcctagcaa    300
tccttggtgg ccggcgcagg gagttgcctg ccgctgccgc acagatgacg aacattgtga    360
ctaaccttgt aaatcatcaa tctaccacag tatggtgtag tgcctggcag tagcggcgtc    420
cagggctacg actatagcag tgcgagtggt atggcttgga ggcatggtca tagctgt       477
```

<210> SEQ ID NO 10
<211> LENGTH: 714
<212> TYPE: DNA
<213> ORGANISM: artificial
<220> FEATURE:
<223> OTHER INFORMATION: PHM10892 reference sequence

<400> SEQUENCE: 10

```
tccaccwtta aattccaatg atgcctggtt ggcaaagagc ccccccattt tggaatggga     60
tacgccgtgc aatatccacc tggagtggta tccatgtcat tctcatatgt gtaacatatt    120
gtgcacctga gttggtactg ccttttttatc ttacacaagg aatactcttc cagttccagg    180
gaatgcaagc atatcctcag cctacatatc agcaacctgt atattcccaa cctgcatatt    240 cccacccca acctgtgaaa gcttcaaacc cttttgatct tgggaatggg ccagctccaa    300
ctcaagctca catggtataa ctaaaatgtc tactgtagac ttgggtagtc tttcatattc    360
tgcattccta gtttgttaac atgtccatta cttctccatt aacatcagtt tgttttctct    420
gtgagcagcc cccatctgga ccaccaggag tattagcagg cccagctccc caaaccttaa    480
ttagcaactc tagttttggt gttccttcac agcagcctca ccagctctat caatcagccg    540
cacatccaag taattgcata ttttcccgtc atgatattgc tctttagtac cttctgtttt    600
ccgcgctgtg ctaattttg tttcaatcag gccatttcat aatgcagcaa gttccgaaca    660
gcatgcccat gcccggaaac gccaaagggg atataaacca aaacccaagg ggcc          714
```

<210> SEQ ID NO 11
<211> LENGTH: 696
<212> TYPE: DNA
<213> ORGANISM: artificial
<220> FEATURE:
<223> OTHER INFORMATION: PHM5273 reference sequence

<400> SEQUENCE: 11

| | | | |
|---|---|---|---|
| caaatgcacc actttacaaa tggaagttga gcwacacttt tgtagggcaa ccaacagaaa | 60 |
| tggagtttta catttcagca gttaagaatc actcataatg tcaataactt tttaacatgt | 120 |
| tatgtgtttt gatttaattc attcctttgt ttatggtatc cctggagatt cttctttggg | 180 |
| ctatgtttct atgtgcgaac ttggtagata tgctggtctg tgctaattct agtagggtta | 240 |
| ctgtttccac attcttccaa ccaattcata cactcaatat tggtatacta acactttga | 300 |
| agaaaagtga gcgcaattgc aaatgtttca aattattatt attggcttgc cgtagcagta | 360 |
| gtgtttatat accacggata tgtgatctgg ttttaagtta acaataacaa cggatgcagg | 420 |
| ttgtgttgtt ttgttgtcct aaatatctgt tactctgatt tttgtactat cagtgaatat | 480 |
| taattgatcg caaactagtg agtgcatgga aatgtgtaat tgacagaatg tatttgtcct | 540 |
| atttggactg cagctaactg tcttaaaatt tgtattttc agtggtgaaa agccatcatt | 600 |
| aaaagattgg cgtagctttg ttgagattaa gggaagagtt aaacttagtg cttttcaaga | 660 |
| atttgtcgag cagctcccaa atctaatttt gttatt | 696 |

<210> SEQ ID NO 12
<211> LENGTH: 649
<212> TYPE: DNA
<213> ORGANISM: artificial
<220> FEATURE:
<223> OTHER INFORMATION: PHM497 reference sequence

<400> SEQUENCE: 12

| | |
|---|---|
| gaactgagat cattcaagaa aaatgaactt gatgcgtggc attgatctga aaagatcgc | 60 |
| ggaaaagatg aatggggcct caggagctga gctcaaggtt tgttaattcc actttatctg | 120 |
| atgaactgcg tgctgcctca tttcaatttt gtgatgtttg cttcttgtc gatccattca | 180 |
| agcagaaaat tatgttcagg catctttta gtcacatctt gcaataatgc ttatgaatac | 240 |
| agagtcgaga attcagaaag cttgcttata agcaatatct tatttgtatt tatttgttta | 300 |
| gcaattttgt tcgtactggc aattttttt ggaattcctt gttataactg ggatttcaat | 360 |
| gcttattacc aagcatttgt gatcgttata gttcctatag ctttgtgttt gtgtttcaga | 420 |
| cttttttcctt tcatttttt ggtgttggtt caggccgtct gcacagaggc tggaatgttt | 480 |
| gctcttcgtg aaagaagggt gcacgttacc caggaggact cgagatggc agtgccaag | 540 |
| gtgatgaaga aagacacgga aagaacatg tccctgcgca agctctggaa ktaaggctcg | 600 |
| tgcccacctt tcacggcctc cccgaagcta ttggcakttc cttcatatc | 649 |

<210> SEQ ID NO 13
<211> LENGTH: 711
<212> TYPE: DNA
<213> ORGANISM: artificial
<220> FEATURE:
<223> OTHER INFORMATION: PHM4483 reference sequence

<400> SEQUENCE: 13

| | |
|---|---|
| gcaagctcgt cccagtcgaa actgggtacg gggtttcgca ccgatcacct cgacggtata | 60 |
| ggagccctct agaggcagag tgtcatcgcc aaggtaaatg aactgtttat agattatagt | 120 |
| taaatatttt tttgtatggt atcaactttt atcatttctg atggcatgtg gcatgctatc | 180 |
| gagccaatta tgaacagaca atcatttttg tttgttactt actctccgtt tcaacttata | 240 |
| agttcttttg actttttga tacatcaatt tactatgtat ctagataaat ctatgtaaaa | 300 |
| aagttaagga gacttattat ttggaatgga tgaagtacta ttttctaatg attgaatcaa | 360 |

```
ttttatttgg attttgtttt ccaatctata tgcgtagctc attcttgtgg ctggttcttt      420
gtttagcagg tacaggagga ggagccgaag cgcatcacgc agtcctgtcc acagaggaag      480
gagaggtggg tacaacaaga gtcctgtacg gagccgttca ccccccgcca ggaaaaggtc      540
acctagcgat cgtgcacggt cagtttccag gagccacctt tttaggtcag tatcaaagtt      600
tccaccagtg catcatccct ccccacttga ttttccattt ttggaaccct caattatggg      660
aaatttcggt cccataaccg tttggtggag gcaaaaaagt tttgtttyyt a               711
```

<210> SEQ ID NO 14
<211> LENGTH: 712
<212> TYPE: DNA
<213> ORGANISM: artificial
<220> FEATURE:
<223> OTHER INFORMATION: PHM2015 reference sequence

<400> SEQUENCE: 14

```
amttgaaccc tttccacctt gamaacaagt ttcatggacg ggcgggggggg attcactgtt      60 tccatgaatc catgtgcttg ttttgttgtc gtacacaagg tctgatggta gttgtacccc     120
tttgtatgct tatgtcttct tgttaagga aaaaaaaggg attgttttat cagcaaacat      180
gctggagtaa gggacaacag aatcgtctgg ctatgctttc tgtctgtctg tcagcatgca    240
tgatatatat tagcaataac ctagcctcaa aatcttctta ggagttgctg atgtctcagt    300
tagttagtgg atgagtaggt aggtaggtac tctgccagta tgcattttgc ttgtgaacac    360
tctgctttct gctaacccctt gtgcgtggct gtgcgaatcg tccacagatc cggatgcaac    420
gagcacaact tcgccagcag gatggagtgc ttcaggtgca acgcaccgcg ggactctggt    480
agcgctgcca tgacctacga aaactacttg taaattaccg aatctttttc ccctcatcgg    540
ccgctctggc tgccatatcc atgacctaac cgagtacggg ttccgtgtgc aggcactgag    600
gtgtaggatc gagcaagtta aaagtctgc agcgccgaag aaagcgacga caagaggagt    660
cctcatcacg tcgtaacgta agagagagag aggagtgaga gagagtagga tg            712
```

<210> SEQ ID NO 15
<211> LENGTH: 523
<212> TYPE: DNA
<213> ORGANISM: artificial
<220> FEATURE:
<223> OTHER INFORMATION: PHM10326 reference sequence

<400> SEQUENCE: 15

```
ttttttataat ttttwttatt aaataaatat attttatgta ttaggggaag gtcccagtca    60
cgacgaaata acgggcttgc tgtcgcgaag agtgagtctt gtctgtaata aagcaaatgt    120
tcatcgagtt ctgttctatt tccatcctaa ccttgctgag aatcaccatg aaggtatcat    180
gacatctact gttgatatca aggacgagac taggacccgg cctatccaga aggccaaggt    240
aaatgtgctt cccatggcca gtggttacac attttcaagt ttatttggtt ggtggactct    300
tttcttacac tcttatatta taatgtgcag attgaaatat tgcttggcaa gacggagaag    360
tttgatgagc tgatggcagc ggctgccgag gagagggagg ctaatggggc cgaggaacaa    420
agctgagtac ctgcaaggaa ggaccttgtt gtagcttatt tactgttttc tgctgctaga    480
tttgtcttct tcatagtttt cgagactttc gtataataat act                      523
```

<210> SEQ ID NO 16
<211> LENGTH: 684
<212> TYPE: DNA

<213> ORGANISM: artificial
<220> FEATURE:
<223> OTHER INFORMATION: PHM9363 reference sequence

<400> SEQUENCE: 16

```
acgttgatgg aggtccttaa ccaattagat ggatttgatg agctaggaaa ggtaaatttg      60
ttatttggat tactcacatt ttttctaggt acaacgatat agtagcttgt gtcttgttgt     120
ttctgtctaa attcagtttg acaaggatat tttggcttga acaggtaaaa atgatcatgg     180
ccacaaatcg acctgatgtt ctggacccgg cgctcctgcg tcctggacgt ttagatagga     240
agattgaaat tccgctaccc aacgagcaat caagaatgga agttctaaaa atccatgcag     300
ccggtatcgc aagcatggg gagattgatt atgaagcagt cgtgaaacta gctgaagtga     360
gttagttgtg ttattcatat ctaacctcta atcccatcct atagtttcac cttactctcc     420
tggtttcagg gtttcaatgg ggctgatctt cggaacgtgt gcaccgaagc tggcatggct     480
gcaattcgtg cagagagaga ttacgtagtc cacgaagact tcatgaaggt gcactatctc     540
gcactccaat cttgtgtacc ttcgaatagt tgtggttaaa cattgacact caaaatccct     600
gcaacttta tttcaggctg tgagaagcta tatgtcaaac tttctttcag gctttaagaa     660
agctttgtgt gcaactttcc ttaa                                            684
```

<210> SEQ ID NO 17
<211> LENGTH: 572
<212> TYPE: DNA
<213> ORGANISM: artificial
<220> FEATURE:
<223> OTHER INFORMATION: PHM18162 reference sequence

<400> SEQUENCE: 17

```
gggaaggtcc cagtcacgac ggtcgacaca ttccgatgga gctagcaata tagtgtcaga      60
tatttgggta gcggacttgg ctggtgaaga ctggatccac ttgcagacta tcatcccct     120
gacgcatctg gcataagcc cgttttttcca gctcaagacg aaggtcttct tcggcaacca     180
gaagagactc ctctgcgtag atcttcagga cggtacggtt tcatacatca acatgccttc     240
cggtgagact ttgatatcct gtggcatgtt tgtggagagc tttgcgcctg ccgcgacagg     300
cctggtgagc tcgactgcgt catatggtga ccgctctcgt ctggctgaac cgtccatggc     360
ggaccctggg ccatctttcc gtggcgcagg gtcatcctcg gcaagccgcg gacggtcttc     420
tggtctcacc ggatggtcct cagctgacct tgagcagtcc ttcaagagaa cgaagaggac     480
gacaaacatg cagtggaaga tatcgaaaca tagagcaatc taggagcgcc tgcatgccta     540
tgataccctc tgagaaattg taaaaaacct ta                                   572
```

<210> SEQ ID NO 18
<211> LENGTH: 692
<212> TYPE: DNA
<213> ORGANISM: artificial
<220> FEATURE:
<223> OTHER INFORMATION: PHM9942 reference sequence

<400> SEQUENCE: 18

```
aggaatatta aggggggttaa taggatccca actatttaac catataatgt tttgccatag      60
cacataacag tgctggcaca tttcttgtaa ccaattttttg cacaggtatt ggacgctgac     120
acagcagcta gcacaccaca ccatcaacgg atgcaacatg aggccggggg atatatttgc     180
gactggcaca ctgagtggac ctgtatggag taaacattgc aacttctata cccatagtat     240
gaatcttact ttgacatgtg ccatttcagg aaccggactc cctcgggtgt ctgctggagc     300
```

```
tgacatggaa cgggcagaag gagataccgg tggggaattt gacccgcaag ttcctagaag    360
atggagatga agtcatcttg acaggatgtt gcaaggtact gtgagttcgg tctttcctga    420
tcaattcaga tctaggcctc tacagtgacg ctaggctgta ttttgattcc accatccgct    480
ggttcttcag ggtgaaggct acaacattgg ttttggaacc tgcaccggga aggttctgcc    540
ggcacttccc tgagccaaca cgtcttggca tcagttctcc ggagtctcaa cgatctcagc    600
tatcagagag ttgtctcaac ggtctcaact atcaaagagt tcatgccgct atctagcaag    660
gctgctatga actaccgaac tttcggtata ta                                  692
```

<210> SEQ ID NO 19
<211> LENGTH: 579
<212> TYPE: DNA
<213> ORGANISM: artificial
<220> FEATURE:
<223> OTHER INFORMATION: PHM5247 reference sequence

<400> SEQUENCE: 19

```
gggaaggtcc cagtcacaac gatgcatgtc gctgaaacca gcgaggctgc tgctgttatc    60
gcgaaggcca aggaaggccc aaaccggtgc gcaacctgta ggaagcgtgt tgggttgacg   120
ggttttaact gccgatgcgg gaacacgtac tgttcgatgc accgctactc cgacaaacac   180
gactgccagt tcgactatcg aactgcagct agggacgcta tcgccaaggc caatccagtg   240
gtgaaggcgg agaagcttga caagatctga ggcggggca ttgggtaacg aaaaatggtt    300
gcgatctgca agaattcagc atgtctcttt gctgctttat cattgaactt cccattcttg   360
tcttgctgtc acgtcccctg gggttcaata ctatgatgcg cacagcatcc tggcagctgc   420
aagaattcat ccccagtcga gtcacgaaaa tggtttgcgt gttggctatg tcgtgtaagc   480
ttattcagtt attcttggtg gtttgggtcg gtaccgtgtc attccccgtt taggtagctc   540
tgtaatctac tattctcatg ggtccaattt gttttttaaa                         579
```

<210> SEQ ID NO 20
<211> LENGTH: 446
<212> TYPE: DNA
<213> ORGANISM: artificial
<220> FEATURE:
<223> OTHER INFORMATION: PHM3985 reference sequence

<400> SEQUENCE: 20

```
agtcaagacg aaattcgggc atagggcagt acgggaaggt cccagtcacg acgaacttcg    60
ggcagtacca cttcgccggc tacttcccca accggccgac caccatccgg aagaacatgc   120
cggtggagga gggcgggccg ggcgaggaga tggagaagtt cctcaagcag ccggagacga   180
cgctgctgga catgctgccc acgcagatgc aaggccatca aggtcatgacg acgctggaca   240 tcctctcgtc gcactcgccc gacgaggagt acatggggga gttcgcggag ccgtcgtggc   300
tggcggagcc catggtgaag gcggcgttcg agaagttcgg cggcaggatg aaggagatcg   360
aggggttcat cgacgagtgc aacaacaacc tgacctcaag aaccgctgcg gcgccggatc   420
gtgccgtacg agtgtgaacc ttcaaa                                        446
```

<210> SEQ ID NO 21
<211> LENGTH: 536
<212> TYPE: DNA
<213> ORGANISM: artificial
<220> FEATURE:
<223> OTHER INFORMATION: PHM6226 reference sequence

```
<400> SEQUENCE: 21
aaggtcccag ttaaaacggg acagaaccaa aacccggata aaccaacagg accaaacaga      60
aattttggga aaatttaggg gccttttttg caagattttt ttttctcag tggcttcagc      120 tccaactccg cagctcaatg tgaaacccta ccaaacggct ccgcatgaaa cgacaacaca     180
ttcacattgc aatcgaagct ctgcagtggc gtctccagcc taacgtagag tgaggctgca     240
gtctggcttc ttttgctaaa gagggcctat gattaacagt tggaaacgac cataacaaaa    300
tagacacaag ttctggcctg gcacacagag atacctatgc aaatcatcag catcaacact    360
tctatggttg aacctaaata gaggattaga tcataggaga acattcaaga acaaacgcag    420
aaaacagatt tagttggcca acagcgaagg gctaaagaag tcagcaaatt tagtagtagg    480
cctgaagcca gcaattcatt agcgtaacct tggggcactt tagctaacct aaggcc        536

<210> SEQ ID NO 22
<211> LENGTH: 719
<212> TYPE: DNA
<213> ORGANISM: artificial
<220> FEATURE:
<223> OTHER INFORMATION: PHM10262 reference sequence

<400> SEQUENCE: 22
cgttgaatta ttcataaaga ttttcctttg aacatcaatg ggcaaaatgc aagcaatttc     60
gacagtgatg gttaatggaa gtttgaatgt tgtatgggtg caaataacat tctacaggca    120
acaatacgcc aaagcataca tgtgtagtat tatagcattg tgccatgtgc aaatataata    180
tatacacttg caccctgaatt ttgtgtgcat ccactattaa aatacttcct gctcacctca   240
ctcgtaccat gctttttagc cactaacttt aatgccttct ttagaatcat ctcacacaaa    300
tgggctctca gccaacgtgt tactgaaaga ggcagctgct aatgcacggg cacaactcga    360
gaaggaaagg aacagcatag agcaatcttt atcaaacata gtagacgtcc aggtaccaac    420
acttacgctt tatgtaacga cttataaatt tatatgtata tactgaccgc gcttgtccat    480
accatccctt gtgtcatgtg tgacatcaga tgaaggaaat ccaagataaa atatgccggt    540
ttgagcagaa ggagatgctg atggagaaag agcggcagca gctccatttt ctaagggatc    600
tacttttcac agaccaattg gcagtcatgc agcatcaaca aaggagtcca gctgtagcca    660
cagagtgcaa gggtgatgag aagccaaagc ccgtgctagc atagttaact ttcgtggaa     719

<210> SEQ ID NO 23
<211> LENGTH: 20
<212> TYPE: DNA
<213> ORGANISM: artificial
<220> FEATURE:
<223> OTHER INFORMATION: PHM12969 external forward primer

<400> SEQUENCE: 23
tgatgaggtg atcgagaagg                                                 20

<210> SEQ ID NO 24
<211> LENGTH: 20
<212> TYPE: DNA
<213> ORGANISM: artificial
<220> FEATURE:
<223> OTHER INFORMATION: PHM12969 internal forward primer

<400> SEQUENCE: 24
aaggccaact gcaccaggta                                                 20
```

```
<210> SEQ ID NO 25
<211> LENGTH: 22
<212> TYPE: DNA
<213> ORGANISM: artificial
<220> FEATURE:
<223> OTHER INFORMATION: PHM12969 internal reverse primer

<400> SEQUENCE: 25
gagtttatat ggtgtactta ac                                              22

<210> SEQ ID NO 26
<211> LENGTH: 21
<212> TYPE: DNA
<213> ORGANISM: artificial
<220> FEATURE:
<223> OTHER INFORMATION: PHM12969 external reverse primer

<400> SEQUENCE: 26
ggctccaagc taaacttgaa t                                               21

<210> SEQ ID NO 27
<211> LENGTH: 21
<212> TYPE: DNA
<213> ORGANISM: artificial
<220> FEATURE:
<223> OTHER INFORMATION: PHM2204 external forward primer

<400> SEQUENCE: 27
aaccaattgc caatacaccg c                                               21

<210> SEQ ID NO 28
<211> LENGTH: 22
<212> TYPE: DNA
<213> ORGANISM: artificial
<220> FEATURE:
<223> OTHER INFORMATION: PHM2204 internal forward primer

<400> SEQUENCE: 28
agttcttgta ttatggagag gt                                              22

<210> SEQ ID NO 29
<211> LENGTH: 20
<212> TYPE: DNA
<213> ORGANISM: artificial
<220> FEATURE:
<223> OTHER INFORMATION: PHM2204 internal reverse primer

<400> SEQUENCE: 29
aaacaagact ggtcctggct                                                 20

<210> SEQ ID NO 30
<211> LENGTH: 20
<212> TYPE: DNA
<213> ORGANISM: artificial
<220> FEATURE:
<223> OTHER INFORMATION: PHM2204 external reverse primer

<400> SEQUENCE: 30
gaatgcctag ctggagatgg                                                 20

<210> SEQ ID NO 31
<211> LENGTH: 20
<212> TYPE: DNA
<213> ORGANISM: artificial
<220> FEATURE:
<223> OTHER INFORMATION: PHM9905 external forward primer
```

```
<400> SEQUENCE: 31
gacgccaaca ccttcttcat                                              20

<210> SEQ ID NO 32
<211> LENGTH: 20
<212> TYPE: DNA
<213> ORGANISM: artificial
<220> FEATURE:
<223> OTHER INFORMATION: PHM9905 internal forward primer

<400> SEQUENCE: 32
tctccgagat cgtcaccaat                                              20

<210> SEQ ID NO 33
<211> LENGTH: 19
<212> TYPE: DNA
<213> ORGANISM: artificial
<220> FEATURE:
<223> OTHER INFORMATION: PHM9905 internal reverse primer

<400> SEQUENCE: 33
acacgacgga gggcaggat                                               19

<210> SEQ ID NO 34
<211> LENGTH: 21
<212> TYPE: DNA
<213> ORGANISM: artificial
<220> FEATURE:
<223> OTHER INFORMATION: PHM9905 external reverse primer

<400> SEQUENCE: 34
ttgaatgcag gatggagcct t                                            21

<210> SEQ ID NO 35
<211> LENGTH: 22
<212> TYPE: DNA
<213> ORGANISM: artificial
<220> FEATURE:
<223> OTHER INFORMATION: PHM12209 external forward primer

<400> SEQUENCE: 35
caacattcca ggttcatgag ta                                           22

<210> SEQ ID NO 36
<211> LENGTH: 22
<212> TYPE: DNA
<213> ORGANISM: artificial
<220> FEATURE:
<223> OTHER INFORMATION: PHM12209 internal forward primer

<400> SEQUENCE: 36
aataattgat ggttctttgt gc                                           22

<210> SEQ ID NO 37
<211> LENGTH: 20
<212> TYPE: DNA
<213> ORGANISM: artificial
<220> FEATURE:
<223> OTHER INFORMATION: PHM12209 internal reverse primer

<400> SEQUENCE: 37
aaacagcttg gtgtatggaa                                              20

<210> SEQ ID NO 38
<211> LENGTH: 22
```

```
<212> TYPE: DNA
<213> ORGANISM: artificial
<220> FEATURE:
<223> OTHER INFORMATION: PHM12209 external reverse primer

<400> SEQUENCE: 38
tacagatacg attagttcca ta                                              22

<210> SEQ ID NO 39
<211> LENGTH: 21
<212> TYPE: DNA
<213> ORGANISM: artificial
<220> FEATURE:
<223> OTHER INFORMATION: PHM13926 external forward primer

<400> SEQUENCE: 39
gtagtagtag ttcatacacg c                                               21

<210> SEQ ID NO 40
<211> LENGTH: 22
<212> TYPE: DNA
<213> ORGANISM: artificial
<220> FEATURE:
<223> OTHER INFORMATION: PHM13926 internal forward primer

<400> SEQUENCE: 40
ccgacatttt tctgtatgta ac                                              22

<210> SEQ ID NO 41
<211> LENGTH: 18
<212> TYPE: DNA
<213> ORGANISM: artificial
<220> FEATURE:
<223> OTHER INFORMATION: PHM13926 internal reverse primer

<400> SEQUENCE: 41
agacagcagg cacgcacg                                                   18

<210> SEQ ID NO 42
<211> LENGTH: 20
<212> TYPE: DNA
<213> ORGANISM: artificial
<220> FEATURE:
<223> OTHER INFORMATION: PHM13926 external reverse primer

<400> SEQUENCE: 42
ttacacgtgg gacgtttgtg                                                 20

<210> SEQ ID NO 43
<211> LENGTH: 20
<212> TYPE: DNA
<213> ORGANISM: artificial
<220> FEATURE:
<223> OTHER INFORMATION: PHM10091 external forward primer

<400> SEQUENCE: 43
acaaggactg gcagaagaag                                                 20

<210> SEQ ID NO 44
<211> LENGTH: 21
<212> TYPE: DNA
<213> ORGANISM: artificial
<220> FEATURE:
<223> OTHER INFORMATION: PHM10091 internal forward primer

<400> SEQUENCE: 44
```
ctagttcact cgaaatctga g                                          21

<210> SEQ ID NO 45
<211> LENGTH: 20
<212> TYPE: DNA
<213> ORGANISM: artificial
<220> FEATURE:
<223> OTHER INFORMATION: PHM10091 internal reverse primer

<400> SEQUENCE: 45
acctcattct ctgtgtggct                                            20

<210> SEQ ID NO 46
<211> LENGTH: 21
<212> TYPE: DNA
<213> ORGANISM: artificial
<220> FEATURE:
<223> OTHER INFORMATION: PHM10091 external reverse primer

<400> SEQUENCE: 46
cttccactgc acgttcatag t                                          21

<210> SEQ ID NO 47
<211> LENGTH: 20
<212> TYPE: DNA
<213> ORGANISM: artificial
<220> FEATURE:
<223> OTHER INFORMATION: PHM18211 external forward primer

<400> SEQUENCE: 47
agatacacga ggcgtaccaa                                            20

<210> SEQ ID NO 48
<211> LENGTH: 19
<212> TYPE: DNA
<213> ORGANISM: artificial
<220> FEATURE:
<223> OTHER INFORMATION: PHM18211 internal forward primer

<400> SEQUENCE: 48
tgtacgacgc cggcatgta                                             19

<210> SEQ ID NO 49
<211> LENGTH: 20
<212> TYPE: DNA
<213> ORGANISM: artificial
<220> FEATURE:
<223> OTHER INFORMATION: PHM18211 internal reverse primer

<400> SEQUENCE: 49
ccttgtggtc tatcttccca                                            20

<210> SEQ ID NO 50
<211> LENGTH: 20
<212> TYPE: DNA
<213> ORGANISM: artificial
<220> FEATURE:
<223> OTHER INFORMATION: PHM18211 external reverse primer

<400> SEQUENCE: 50
ccttgtgggt ggagattcta                                            20

<210> SEQ ID NO 51
<211> LENGTH: 18
<212> TYPE: DNA
<213> ORGANISM: artificial

<220> FEATURE:
<223> OTHER INFORMATION: PHM1695 external forward primer

<400> SEQUENCE: 51
tgacccgctt cgcccgcg         18

<210> SEQ ID NO 52
<211> LENGTH: 18
<212> TYPE: DNA
<213> ORGANISM: artificial
<220> FEATURE:
<223> OTHER INFORMATION: PHM1695 internal forward primer

<400> SEQUENCE: 52
tcctactccg cgctccgc         18

<210> SEQ ID NO 53
<211> LENGTH: 20
<212> TYPE: DNA
<213> ORGANISM: artificial
<220> FEATURE:
<223> OTHER INFORMATION: PHM1695 internal reverse primer

<400> SEQUENCE: 53
aactctgaca agtgcccagt         20

<210> SEQ ID NO 54
<211> LENGTH: 20
<212> TYPE: DNA
<213> ORGANISM: artificial
<220> FEATURE:
<223> OTHER INFORMATION: PHM1695 external reverse primer

<400> SEQUENCE: 54
tcgcgcatcc aaccaaacta         20

<210> SEQ ID NO 55
<211> LENGTH: 18
<212> TYPE: DNA
<213> ORGANISM: artificial
<220> FEATURE:
<223> OTHER INFORMATION: PHM939 external forward primer

<400> SEQUENCE: 55
ctgacgatgc ccctccgg         18

<210> SEQ ID NO 56
<211> LENGTH: 20
<212> TYPE: DNA
<213> ORGANISM: artificial
<220> FEATURE:
<223> OTHER INFORMATION: PHM939 internal forward primer

<400> SEQUENCE: 56
gcagagcaaa tgagggaact         20

<210> SEQ ID NO 57
<211> LENGTH: 19
<212> TYPE: DNA
<213> ORGANISM: artificial
<220> FEATURE:
<223> OTHER INFORMATION: PHM939 internal reverse primer

<400> SEQUENCE: 57
gcctccaagc cataccact         19

```
<210> SEQ ID NO 58
<211> LENGTH: 22
<212> TYPE: DNA
<213> ORGANISM: artificial
<220> FEATURE:
<223> OTHER INFORMATION: PHM939 external reverse primer

<400> SEQUENCE: 58
actatctagt ccatccagat ta                                              22

<210> SEQ ID NO 59
<211> LENGTH: 21
<212> TYPE: DNA
<213> ORGANISM: artificial
<220> FEATURE:
<223> OTHER INFORMATION: PHM10892 external forward primer

<400> SEQUENCE: 59
catctcaagc tactgcaaag c                                               21

<210> SEQ ID NO 60
<211> LENGTH: 22
<212> TYPE: DNA
<213> ORGANISM: artificial
<220> FEATURE:
<223> OTHER INFORMATION: PHM10892 internal forward primer

<400> SEQUENCE: 60
gcttcttcta ctgacagtaa at                                              22

<210> SEQ ID NO 61
<211> LENGTH: 20
<212> TYPE: DNA
<213> ORGANISM: artificial
<220> FEATURE:
<223> OTHER INFORMATION: PHM10892 internal reverse primer

<400> SEQUENCE: 61
ttaggttgtt gctcgggcat                                                 20

<210> SEQ ID NO 62
<211> LENGTH: 20
<212> TYPE: DNA
<213> ORGANISM: artificial
<220> FEATURE:
<223> OTHER INFORMATION: PHM10892 external reverse primer

<400> SEQUENCE: 62
tgctgcagac ccttagtcta                                                 20

<210> SEQ ID NO 63
<211> LENGTH: 21
<212> TYPE: DNA
<213> ORGANISM: artificial
<220> FEATURE:
<223> OTHER INFORMATION: PHM5273 external forward primer

<400> SEQUENCE: 63
tccagagaca gaggataatg c                                               21

<210> SEQ ID NO 64
<211> LENGTH: 22
<212> TYPE: DNA
<213> ORGANISM: artificial
<220> FEATURE:
<223> OTHER INFORMATION: PHM5273 internal forward primer
```

<400> SEQUENCE: 64
caccagagaa atttgaatct ga                                              22

<210> SEQ ID NO 65
<211> LENGTH: 20
<212> TYPE: DNA
<213> ORGANISM: artificial
<220> FEATURE:
<223> OTHER INFORMATION: PHM5273 internal reverse primer

<400> SEQUENCE: 65
ctagatttgg gaagctgctc                                                 20

<210> SEQ ID NO 66
<211> LENGTH: 22
<212> TYPE: DNA
<213> ORGANISM: artificial
<220> FEATURE:
<223> OTHER INFORMATION: PHM5273 external reverse primer

<400> SEQUENCE: 66
tcagttatca ttatagcacg gc                                              22

<210> SEQ ID NO 67
<211> LENGTH: 18
<212> TYPE: DNA
<213> ORGANISM: artificial
<220> FEATURE:
<223> OTHER INFORMATION: PHM497 external forward primer

<400> SEQUENCE: 67
agcccttctg aggcctgg                                                   18

<210> SEQ ID NO 68
<211> LENGTH: 22
<212> TYPE: DNA
<213> ORGANISM: artificial
<220> FEATURE:
<223> OTHER INFORMATION: PHM497 internal forward primer

<400> SEQUENCE: 68
gtttcgatat cttgaagatc ca                                              22

<210> SEQ ID NO 69
<211> LENGTH: 21
<212> TYPE: DNA
<213> ORGANISM: artificial
<220> FEATURE:
<223> OTHER INFORMATION: PHM497 internal reverse primer

<400> SEQUENCE: 69
accattatgc agtgtccaca t                                               21

<210> SEQ ID NO 70
<211> LENGTH: 21
<212> TYPE: DNA
<213> ORGANISM: artificial
<220> FEATURE:
<223> OTHER INFORMATION: PHM497 external reverse primer

<400> SEQUENCE: 70
acgagaatgt ggataatccg a                                               21

<210> SEQ ID NO 71

```
<211> LENGTH: 22
<212> TYPE: DNA
<213> ORGANISM: artificial
<220> FEATURE:
<223> OTHER INFORMATION: PHM4483 external forward primer

<400> SEQUENCE: 71
caacgctatt catttgcaag ac                                             22

<210> SEQ ID NO 72
<211> LENGTH: 20
<212> TYPE: DNA
<213> ORGANISM: artificial
<220> FEATURE:
<223> OTHER INFORMATION: PHM4483 internal forward primer

<400> SEQUENCE: 72
gacagataca tgggttaccg                                                20

<210> SEQ ID NO 73
<211> LENGTH: 21
<212> TYPE: DNA
<213> ORGANISM: artificial
<220> FEATURE:
<223> OTHER INFORMATION: PHM4483 internal reverse primer

<400> SEQUENCE: 73
ccgttctctt ctctacagta g                                              21

<210> SEQ ID NO 74
<211> LENGTH: 22
<212> TYPE: DNA
<213> ORGANISM: artificial
<220> FEATURE:
<223> OTHER INFORMATION: PHM4483 external reverse primer

<400> SEQUENCE: 74
aagataatct aaggacaacg ac                                             22

<210> SEQ ID NO 75
<211> LENGTH: 19
<212> TYPE: DNA
<213> ORGANISM: artificial
<220> FEATURE:
<223> OTHER INFORMATION: PHM2015 external forward primer

<400> SEQUENCE: 75
gccagcacct caacttcag                                                 19

<210> SEQ ID NO 76
<211> LENGTH: 20
<212> TYPE: DNA
<213> ORGANISM: artificial
<220> FEATURE:
<223> OTHER INFORMATION: PHM2015 internal forward primer

<400> SEQUENCE: 76
gacatatgcc agcgctgtag                                                20

<210> SEQ ID NO 77
<211> LENGTH: 22
<212> TYPE: DNA
<213> ORGANISM: artificial
<220> FEATURE:
<223> OTHER INFORMATION: PHM2015 internal reverse primer

<400> SEQUENCE: 77
```

```
tttggcaaat ccactactct ct                                              22

<210> SEQ ID NO 78
<211> LENGTH: 19
<212> TYPE: DNA
<213> ORGANISM: artificial
<220> FEATURE:
<223> OTHER INFORMATION: PHM2015 external reverse primer

<400> SEQUENCE: 78
agagcatcgc ggccgtctt                                                  19

<210> SEQ ID NO 79
<211> LENGTH: 20
<212> TYPE: DNA
<213> ORGANISM: artificial
<220> FEATURE:
<223> OTHER INFORMATION: PHM10326 external forward primer

<400> SEQUENCE: 79
gccgtgaaca acctcaacat                                                 20

<210> SEQ ID NO 80
<211> LENGTH: 20
<212> TYPE: DNA
<213> ORGANISM: artificial
<220> FEATURE:
<223> OTHER INFORMATION: PHM10326 internal forward primer

<400> SEQUENCE: 80
aaataacggg cttgctgtcg                                                 20

<210> SEQ ID NO 81
<211> LENGTH: 21
<212> TYPE: DNA
<213> ORGANISM: artificial
<220> FEATURE:
<223> OTHER INFORMATION: PHM10326 internal reverse primer

<400> SEQUENCE: 81
ccactcgaca aactatgaag a                                               21

<210> SEQ ID NO 82
<211> LENGTH: 21
<212> TYPE: DNA
<213> ORGANISM: artificial
<220> FEATURE:
<223> OTHER INFORMATION: PHM10326 external reverse primer

<400> SEQUENCE: 82
aaagcacact aaataagccg c                                               21

<210> SEQ ID NO 83
<211> LENGTH: 21
<212> TYPE: DNA
<213> ORGANISM: artificial
<220> FEATURE:
<223> OTHER INFORMATION: PHM9363 external forward primer

<400> SEQUENCE: 83
catgcatcat cttcatggat g                                               21

<210> SEQ ID NO 84
<211> LENGTH: 20
<212> TYPE: DNA
```

```
<213> ORGANISM: artificial
<220> FEATURE:
<223> OTHER INFORMATION: PHM9363 internal forward primer

<400> SEQUENCE: 84
gacgttgatg gagctcctta                                                     20

<210> SEQ ID NO 85
<211> LENGTH: 21
<212> TYPE: DNA
<213> ORGANISM: artificial
<220> FEATURE:
<223> OTHER INFORMATION: PHM9363 internal reverse primer

<400> SEQUENCE: 85
tttgcatcat ttagcttcct c                                                   21

<210> SEQ ID NO 86
<211> LENGTH: 20
<212> TYPE: DNA
<213> ORGANISM: artificial
<220> FEATURE:
<223> OTHER INFORMATION: PHM9363 external reverse primer

<400> SEQUENCE: 86
taatgcgcac tcgattccag                                                     20

<210> SEQ ID NO 87
<211> LENGTH: 20
<212> TYPE: DNA
<213> ORGANISM: artificial
<220> FEATURE:
<223> OTHER INFORMATION: PHM18162 external forward primer

<400> SEQUENCE: 87
atgttgtcaa gctccgcagt                                                     20

<210> SEQ ID NO 88
<211> LENGTH: 20
<212> TYPE: DNA
<213> ORGANISM: artificial
<220> FEATURE:
<223> OTHER INFORMATION: PHM18162 internal forward primer

<400> SEQUENCE: 88
gtcgacacat tccgatggat                                                     20

<210> SEQ ID NO 89
<211> LENGTH: 22
<212> TYPE: DNA
<213> ORGANISM: artificial
<220> FEATURE:
<223> OTHER INFORMATION: PHM18162 internal reverse primer

<400> SEQUENCE: 89
acagtctaga gggtaatcca ta                                                  22

<210> SEQ ID NO 90
<211> LENGTH: 22
<212> TYPE: DNA
<213> ORGANISM: artificial
<220> FEATURE:
<223> OTHER INFORMATION: PHM18162 external reverse primer

<400> SEQUENCE: 90
cccttgatct tgacatttat tg                                                  22
```

```
<210> SEQ ID NO 91
<211> LENGTH: 20
<212> TYPE: DNA
<213> ORGANISM: artificial
<220> FEATURE:
<223> OTHER INFORMATION: PHM9942 external forward primer

<400> SEQUENCE: 91
gcctggatta agccgaaaga                                              20

<210> SEQ ID NO 92
<211> LENGTH: 22
<212> TYPE: DNA
<213> ORGANISM: artificial
<220> FEATURE:
<223> OTHER INFORMATION: PHM9942 internal forward primer

<400> SEQUENCE: 92
aatgacgcat caattgtcac aa                                           22

<210> SEQ ID NO 93
<211> LENGTH: 22
<212> TYPE: DNA
<213> ORGANISM: artificial
<220> FEATURE:
<223> OTHER INFORMATION: PHM9942 internal reverse primer

<400> SEQUENCE: 93
tattgttcag ttacatagca gc                                           22

<210> SEQ ID NO 94
<211> LENGTH: 21
<212> TYPE: DNA
<213> ORGANISM: artificial
<220> FEATURE:
<223> OTHER INFORMATION: PHM9942 external reverse primer

<400> SEQUENCE: 94
gcatcagtct cctcatcttc a                                            21

<210> SEQ ID NO 95
<211> LENGTH: 20
<212> TYPE: DNA
<213> ORGANISM: artificial
<220> FEATURE:
<223> OTHER INFORMATION: PHM5247 external forward primer

<400> SEQUENCE: 95
aaaggacctg caattgctgc                                              20

<210> SEQ ID NO 96
<211> LENGTH: 20
<212> TYPE: DNA
<213> ORGANISM: artificial
<220> FEATURE:
<223> OTHER INFORMATION: PHM5247 internal forward primer

<400> SEQUENCE: 96
atgcatgtcg ctgaaaccag                                              20

<210> SEQ ID NO 97
<211> LENGTH: 22
<212> TYPE: DNA
<213> ORGANISM: artificial
<220> FEATURE:
```

```
<223> OTHER INFORMATION: PHM5247 internal reverse primer

<400> SEQUENCE: 97
ggcaacacac atgagaatag ta                                              22

<210> SEQ ID NO 98
<211> LENGTH: 22
<212> TYPE: DNA
<213> ORGANISM: artificial
<220> FEATURE:
<223> OTHER INFORMATION: PHM5247 external forward primer

<400> SEQUENCE: 98
gctgattact attactgatt gg                                              22

<210> SEQ ID NO 99
<211> LENGTH: 20
<212> TYPE: DNA
<213> ORGANISM: artificial
<220> FEATURE:
<223> OTHER INFORMATION: PHM3985 external forward primer

<400> SEQUENCE: 99
tccgagtacg tcaacgtcta                                                 20

<210> SEQ ID NO 100
<211> LENGTH: 20
<212> TYPE: DNA
<213> ORGANISM: artificial
<220> FEATURE:
<223> OTHER INFORMATION: PHM3985 internal forward primer

<400> SEQUENCE: 100
aacttcgggc agtaccactt                                                 20

<210> SEQ ID NO 101
<211> LENGTH: 19
<212> TYPE: DNA
<213> ORGANISM: artificial
<220> FEATURE:
<223> OTHER INFORMATION: PHM3985 internal reverse primer

<400> SEQUENCE: 101
ttggagaagg gcttgagca                                                  19

<210> SEQ ID NO 102
<211> LENGTH: 22
<212> TYPE: DNA
<213> ORGANISM: artificial
<220> FEATURE:
<223> OTHER INFORMATION: PHM3985 external reverse primer

<400> SEQUENCE: 102
ctgcatgcaa taatagtaca ac                                              22

<210> SEQ ID NO 103
<211> LENGTH: 18
<212> TYPE: DNA
<213> ORGANISM: artificial
<220> FEATURE:
<223> OTHER INFORMATION: PHM6226 external forward primer

<400> SEQUENCE: 103
ggaggctgat ttgcggat                                                   18
```

```
<210> SEQ ID NO 104
<211> LENGTH: 18
<212> TYPE: DNA
<213> ORGANISM: artificial
<220> FEATURE:
<223> OTHER INFORMATION: PHM6226 internal forward primer

<400> SEQUENCE: 104
gaacagaacc aacacccg                                              18

<210> SEQ ID NO 105
<211> LENGTH: 19
<212> TYPE: DNA
<213> ORGANISM: artificial
<220> FEATURE:
<223> OTHER INFORMATION: PHM6226 internal reverse primer

<400> SEQUENCE: 105
ggcttcttta ggtctacgc                                             19

<210> SEQ ID NO 106
<211> LENGTH: 18
<212> TYPE: DNA
<213> ORGANISM: artificial
<220> FEATURE:
<223> OTHER INFORMATION: PHM6226 external reverse primer

<400> SEQUENCE: 106
ctgccgctgc ttgagatc                                              18

<210> SEQ ID NO 107
<211> LENGTH: 19
<212> TYPE: DNA
<213> ORGANISM: artificial
<220> FEATURE:
<223> OTHER INFORMATION: PHM10262 external forward primer

<400> SEQUENCE: 107
gatagaatga ggtttgaga                                             19

<210> SEQ ID NO 108
<211> LENGTH: 21
<212> TYPE: DNA
<213> ORGANISM: artificial
<220> FEATURE:
<223> OTHER INFORMATION: PHM10262 internal forward primer

<400> SEQUENCE: 108
tgttgacttt aatgacggcg a                                          21

<210> SEQ ID NO 109
<211> LENGTH: 21
<212> TYPE: DNA
<213> ORGANISM: artificial
<220> FEATURE:
<223> OTHER INFORMATION: PHM10262 internal reverse primer

<400> SEQUENCE: 109
tatcaactca tgctagccac g                                          21

<210> SEQ ID NO 110
<211> LENGTH: 21
<212> TYPE: DNA
<213> ORGANISM: artificial
<220> FEATURE:
<223> OTHER INFORMATION: PHM10262 external reverse primer
```

<400> SEQUENCE: 110
atgctacgct gaggatctac t                                              21

<210> SEQ ID NO 111
<211> LENGTH: 32
<212> TYPE: DNA
<213> ORGANISM: artificial
<220> FEATURE:
<223> OTHER INFORMATION: PHM12209-20-U primer 1

<400> SEQUENCE: 111
tgatggatta agagtagcaa ctggttccta ca                                  32

<210> SEQ ID NO 112
<211> LENGTH: 23
<212> TYPE: DNA
<213> ORGANISM: artificial
<220> FEATURE:
<223> OTHER INFORMATION: PHM12209-20-U primer 2

<400> SEQUENCE: 112
gcctcactgt taccagtacc gca                                            23

<210> SEQ ID NO 113
<211> LENGTH: 26
<212> TYPE: DNA
<213> ORGANISM: artificial
<220> FEATURE:
<223> OTHER INFORMATION: PHM12209-20-U probe 1

<400> SEQUENCE: 113
cgcgccgagg gctggacgag catatg                                         26

<210> SEQ ID NO 114
<211> LENGTH: 29
<212> TYPE: DNA
<213> ORGANISM: artificial
<220> FEATURE:
<223> OTHER INFORMATION: PHM12209-20-U probe 2

<400> SEQUENCE: 114
acggacgcgg agactggacg agcatatga                                      29

<210> SEQ ID NO 115
<211> LENGTH: 32
<212> TYPE: DNA
<213> ORGANISM: artificial
<220> FEATURE:
<223> OTHER INFORMATION: PHM12209-21-U primer 1

<400> SEQUENCE: 115
tctcatatgc tcgtccagyt gtaatacagc tt                                  32

<210> SEQ ID NO 116
<211> LENGTH: 27
<212> TYPE: DNA
<213> ORGANISM: artificial
<220> FEATURE:
<223> OTHER INFORMATION: PHM12209-21-U primer 2

<400> SEQUENCE: 116
aacggcaacc aaacacrcga aaaatgt                                        27

<210> SEQ ID NO 117
<211> LENGTH: 31

<210> SEQ ID NO 117
<211> LENGTH: 31
<212> TYPE: DNA
<213> ORGANISM: artificial
<220> FEATURE:
<223> OTHER INFORMATION: PHM12209-21-U probe 1

<400> SEQUENCE: 117
cgcgccgagg ttaactagct gtttgtgatc t                                31

<210> SEQ ID NO 118
<211> LENGTH: 33
<212> TYPE: DNA
<213> ORGANISM: artificial
<220> FEATURE:
<223> OTHER INFORMATION: PHM12209-21-U probe 2

<400> SEQUENCE: 118
acggacgcgg agctaactag ctgtttgtga tct                              33

<210> SEQ ID NO 119
<211> LENGTH: 34
<212> TYPE: DNA
<213> ORGANISM: artificial
<220> FEATURE:
<223> OTHER INFORMATION: PHM12209-23-U primer 1

<400> SEQUENCE: 119
ggctccatta acaggaayta actagctgtt tgtg                             34

<210> SEQ ID NO 120
<211> LENGTH: 26
<212> TYPE: DNA
<213> ORGANISM: artificial
<220> FEATURE:
<223> OTHER INFORMATION: PHM12209-23-U primer 2

<400> SEQUENCE: 120
gcttcaagtg ttgttgcttc actgct                                      26

<210> SEQ ID NO 121
<211> LENGTH: 29
<212> TYPE: DNA
<213> ORGANISM: artificial
<220> FEATURE:
<223> OTHER INFORMATION: PHM12209-23-U probe 1

<400> SEQUENCE: 121
cgcgccgagg acgaaaaatg ttgctgaag                                   29

<210> SEQ ID NO 122
<211> LENGTH: 30
<212> TYPE: DNA
<213> ORGANISM: artificial
<220> FEATURE:
<223> OTHER INFORMATION: PHM12209-23-U probe 2

<400> SEQUENCE: 122
acggacgcgg aggcgaaaaa tgttgctgaa                                  30

<210> SEQ ID NO 123
<211> LENGTH: 32
<212> TYPE: DNA
<213> ORGANISM: artificial
<220> FEATURE:
<223> OTHER INFORMATION: PHM10892-3-U primer 1

<400> SEQUENCE: 123

```
gctccaactc aagctcacat ggtataacta aa                                         32

<210> SEQ ID NO 124
<211> LENGTH: 35
<212> TYPE: DNA
<213> ORGANISM: artificial
<220> FEATURE:
<223> OTHER INFORMATION: PHM10892-3-U primer 2

<400> SEQUENCE: 124
ggctgctcac agaraaaaca aactgatgtt aatgg                                      35

<210> SEQ ID NO 125
<211> LENGTH: 31
<212> TYPE: DNA
<213> ORGANISM: artificial
<220> FEATURE:
<223> OTHER INFORMATION: PHM10892-3-U probe 1

<400> SEQUENCE: 125
cgcgccgagg gactaggaat gcagaatatg a                                          31

<210> SEQ ID NO 126
<211> LENGTH: 33
<212> TYPE: DNA
<213> ORGANISM: artificial
<220> FEATURE:
<223> OTHER INFORMATION: PHM10892-3-U probe 2

<400> SEQUENCE: 126
acggacgcgg agaactagga atgcagaata tga                                        33
```

US 9,060,477 B2

GENETIC LOCI ON MAIZE CHROMOSOMES 3 AND 4 THAT ARE ASSOCIATED WITH FUSARIUM EAR MOLD RESISTANCE

CROSS-REFERENCE TO RELATED APPLICATION

This application claims the benefit of U.S. Provisional Application No. 61/298,233, filed Jan. 26, 2010, which is herein incorporated by reference in its entirety.

FIELD OF THE INVENTION

The present disclosure relates to compositions and methods useful in enhancing resistance to *Fusarium* ear mold in maize plants.

BACKGROUND OF THE INVENTION

*Fusarium* ear mold (also referred to as *Fusarium* ear rot) is a devastating disease of maize caused by species of the *Gibberella fuijkuroi* complex, namely *F. verticillioides, F. proliferatum*, and/or *F. subglutinans*. It is predominantly found in the southeastern United States, southern Europe, Mexico, Brazil, Argentina, and South Africa, and affects both grain yield and quality. *Fusarium* ear mold can also result in contamination by several mycotoxins, including fumonisins (FUM), moniliformin (MON), and/or beauvericin, which appear to cause a number of human and animal diseases. Fumonisins, e.g., are linked to several animal toxicoses including leukoencephalomalacia (Marasas et al. (1988) *Onderstepoort J. Vet. Res.* 55:197-204; Wilson et al. (1990) *American Association of Veterinary Laboratory Diagnosticians: Abstracts* 33rd Annual Meeting, Denver, Colo., Madison, Wis., USA) and porcine pulmonary edema (Colvin et al. (1992) *Mycopathologia* 117:79-82). Fumonisins are also suspected carcinogens (Geary et al. (1971) *Coord. Chem. Rev.* 7:81; Gelderblom et al. (1991) *Carcinogenesis* 12:1247-1251; Gelderblom et al. (1992) *Carcinogenesis* 13:433-437) and have been linked to birth defects in humans (Missmer et al. (2006) *Environ Health perspect* 114:237-41).

The use of phenotypic selection to introgress *Fusarium* ear mold resistance into susceptible lines is time consuming and difficult, and since *Fusarium* ear mold is sensitive to environmental conditions, selection for resistance from year to year based solely on phenotype has proven unreliable. In addition, specialized disease screening sites can be costly to operate, and plants must be grown to maturity in order to classify the level of resistance or susceptibility.

Selection through the use of molecular markers associated with *Fusarium* ear mold resistance, however, has the advantage of permitting at least some selection based solely on the genetic composition of the progeny. Moreover, resistance to *Fusarium* ear mold can be determined very early on in the plant life cycle, even as early as the seed stage. The increased rate of selection that can be obtained through the use of molecular markers associated with the *Fusarium* ear mold resistance trait means that plant breeding for *Fusarium* ear mold resistance can occur more rapidly, thereby generating commercially acceptable resistant plants in a relatively short amount of time. Thus, it is desirable to provide compositions and methods for identifying and selecting maize plants with enhanced resistance to *Fusarium* ear mold.

Some instances of genetic resistance to *Fusarium* ear mold have been reported (Perez-Brito et al. (2001) *Agrociencia* 35:181-196; Ali et al. (2005) *Genome* 48:521-533; Robertson-Hoyt et al. (2006) *Crop Sci.* 46:1734-1743; Zhang et al. (2005) *J Appl Genet* 47:9-15; Robertson-Hoyt et al. (2007) *Phytopathology* 97:311-317; Ding et al. (2008) *Mol Breeding* 22:395-403).

SUMMARY

Compositions and methods for identifying and selecting maize plants with enhanced resistance to *Fusarium* ear mold are provided.

In one embodiment, methods of selecting a maize plant with enhanced resistance to *Fusarium* ear mold are provided. In these methods, the presence of at least one marker allele is detected in a maize plant. The marker allele can include any marker allele that is linked to and associated with any of the following marker alleles: a "C" at PHM12209.11, a "T" at PHM12209.20, a "C" at PHM12209.21, a "G" at PHM12209.22, a "C" at PHM12209.23, an "A" at PHM9905.11, a "T" at PHM9905.13, a "G" at PHM9905.35, a "T" at PHM2204.88, an "A" at PHM2204.105, a "C" at PHM13926.25, a "G" at PHM13926.27, a "G" at PHM13926.28, a "G" at PHM13926.32, a "C" at PHM10892.3, a "G" at PHM939.47, and an "A" at PHM939.48. A maize plant that has the marker allele linked to and associated with any of the marker alleles listed above is then selected.

In other embodiments, the marker allele can be linked to any of the following marker alleles: a "C" at PHM12209.11, a "T" at PHM12209.20, a "C" at PHM12209.21, a "G" at PHM12209.22, a "C" at PHM12209.23, an "A" at PHM9905.11, a "T" at PHM9905.13, a "G" at PHM9905.35, a "T" at PHM2204.88, an "A" at PHM2204.105, a "C" at PHM13926.25, a "G" at PHM13926.27, a "G" at PHM13926.28, a "G" at PHM13926.32, a "C" at PHM10892.3, a "G" at PHM939.47, and an "A" at PHM939.48 by 30 cM, 25, 20, 15, 10, 9, 8, 7, 6, 5, 4, 3, 2, 1, 0.9, 0.8, 0.7, 0.6, 0.5, 0.4, 0.3, 0.2, or 0.1 cM based on a single meiosis map.

In another embodiment, methods of selecting a maize plant with enhanced resistance to *Fusarium* ear mold are provided. In these methods, the presence of at least one marker allele is detected in a maize plant. The marker allele can be any of the following marker alleles: a "C" at PHM12209.11, a "T" at PHM12209.20, a "C" at PHM12209.21, a "G" at PHM12209.22, a "C" at PHM12209.23, an "A" at PHM9905.11, a "T" at PHM9905.13, a "G" at PHM9905.35, a "T" at PHM2204.88, an "A" at PHM2204.105, a "C" at PHM13926.25, a "G" at PHM13926.27, a "G" at PHM13926.28, a "G" at PHM13926.32, a "C" at PHM10892.3, a "G" at PHM939.47, and an "A" at PHM939.48. A maize plant that has at least one of the marker alleles listed above is then selected.

In another embodiment, methods for identifying maize plants with enhanced resistance to *Fusarium* ear mold by detecting a marker locus in a maize plant using the sequence of the marker locus, a portion of the sequence of the marker locus, or a complement of the sequence of the marker locus, or of a portion thereof, as a marker probe, are provided. In these methods, the marker probe hybridizes under stringent conditions to the contiguous DNA between and including SEQ ID NO:1, or a nucleotide sequence that is 95% identical to SEQ ID NO:1 based on the Clustal V method of alignment, and SEQ ID NO:7, or a nucleotide sequence that is 95% identical to SEQ ID NO:7 based on the Clustal V method of alignment, and the marker locus comprises at least one allele that is associated with the enhanced resistance to *Fusarium* ear mold. Maize plants that have at least one allele associated with enhanced resistance to *Fusarium* ear mold are then selected.

In another embodiment, methods for selecting maize plants with enhanced resistance to *Fusarium* ear mold by detecting at least one marker locus in a first maize plant, crossing the first maize plant to a second maize plant, evaluating the progeny at the at least one marker locus, and selecting the progeny plants that have the same allele at the at least one marker locus as the first maize plant, are provided. The marker locus can be detected using the sequence of the marker locus, a portion of the sequence of the marker locus, or a complement of the sequence of the marker locus, or of a portion thereof, as a marker probe. The marker probe hybridizes under stringent conditions to the contiguous DNA between and including SEQ ID NO:1, or a nucleotide sequence that is 95% identical to SEQ ID NO:1 based on the Clustal V method of alignment, and SEQ ID NO:7, or a nucleotide sequence that is 95% identical to SEQ ID NO:7 based on the Clustal V method of alignment, and the marker locus comprises at least one allele that is associated with enhanced resistance to *Fusarium* ear mold.

In another embodiment, methods for identifying maize plants with enhanced to resistance to *Fusarium* ear mold by detecting a marker locus in a maize plant using the sequence of the marker locus, a portion of the sequence of the marker locus, or a complement of the sequence of the marker locus, or of a portion thereof, as a marker probe, are provided. In these methods, the marker probe hybridizes under stringent conditions to the contiguous DNA between and including SEQ ID NO:10, or a nucleotide sequence that is 95% identical to SEQ ID NO:10 based on the Clustal V method of alignment, and SEQ ID NO:22, or a nucleotide sequence that is 95% identical to SEQ ID NO:22 based on the Clustal V method of alignment, and the marker locus comprises at least one allele that is associated with enhanced resistance to *Fusarium* ear mold. Maize plants that have at least one allele associated with enhanced resistance to *Fusarium* ear mold are then selected.

In another embodiment, methods for selecting maize plants with enhanced resistance to *Fusarium* ear mold by detecting at least one marker locus in a first maize plant, crossing the first maize plant to a second maize plant, evaluating the progeny at the at least one marker locus, and selecting the progeny plants that have the same allele at the at least one marker locus as the first maize plant, are provided. The marker locus can be detected using the sequence of the marker locus, a portion of the sequence of the marker locus, or a complement of the sequence of the marker locus, or of a portion thereof, as a marker probe. The marker probe hybridizes under stringent conditions to the contiguous DNA between and including SEQ ID NO:10, or a nucleotide sequence that is 95% identical to SEQ ID NO:10 based on the Clustal V method of alignment, and SEQ ID NO:22, or a nucleotide sequence that is 95% identical to SEQ ID NO:22 based on the Clustal V method of alignment, and the marker locus comprises at least one allele that is associated with enhanced resistance to *Fusarium* ear mold.

In another embodiment, methods for identifying maize plants with enhanced resistance to *Fusarium* ear mold by detecting at least one marker allele associated with the enhanced resistance in the maize plant are provided. The marker locus can be selected from any of the following marker loci: PHM12969, PHM1695, PHM12209, PHM2204, PHM9905, PHM13926, PHM10091, and PHM18211, as well as any other marker that is linked to these markers, and the marker locus can be found within the interval on chromosome 3 comprising and flanked by PHM12969 and PHM18211. The marker locus comprises at least one allele that is associated with enhanced resistance to *Fusarium* ear mold.

In another embodiment, methods of selecting maize plants with enhanced resistance to *Fusarium* ear mold are provided. In one aspect, a first maize plant is obtained that has at least one allele of a marker locus wherein the allele is associated with enhanced resistance to *Fusarium* ear mold. The marker locus can be found within the interval on chromosome 3 comprising and flanked by PHM12969 and PHM18211. The first maize plant can then be crossed to a second maize plant, and the progeny plants resulting from the cross can be evaluated for the allele of the first maize plant. Progeny plants that possess the allele of the first maize plant can be selected as having enhanced resistance to *Fusarium* ear mold.

In another embodiment, methods for identifying maize plants with enhanced resistance to *Fusarium* ear mold by detecting at least one marker allele associated with the enhanced resistance in the maize plant are provided. The marker locus can be selected from any of the following marker loci: PHM2015, PHM10326, PHM497, PHM4483, PHM5273, PHM939, PHM10892, PHM9363, PHM18162, PHM9942, PHM5247, PHM3985, PHM6226, and PHM10262, as well as any other marker that is linked to these markers, and the marker locus can be found within the interval on chromosome 4 comprising and flanked by PHM10892 and PHM10262. The marker locus comprises at least one allele that is associated with enhanced resistance to *Fusarium* ear mold.

In another embodiment, methods of selecting maize plants with enhanced resistance to *Fusarium* ear mold are provided. In one aspect, a first maize plant is obtained that has at least one allele of a marker locus wherein the allele is associated with enhanced resistance to *Fusarium* ear mold. The marker locus can be found within the chromosomal interval comprising and flanked by PHM10892 and PHM10262. The first maize plant can be crossed to a second maize plant, and the progeny plants resulting from the cross can be evaluated for the allele of the first maize plant. Progeny plants that possess the allele of the first maize plant can be selected as having enhanced resistance to *Fusarium* ear mold.

In another embodiment, methods for identifying maize plants with enhanced resistance to *Fusarium* ear mold by detecting alleles at two separate marker loci are provided. The first marker locus is located within an interval on chromosome 3 comprising and flanked by PHM12969 and PHM18211, and the second marker locus is located within an interval on chromosome 4 comprising and flanked by PHM10892 and PHM10262. Each marker locus comprises at least one allele that is associated with enhanced resistance to *Fusarium* ear mold.

In another embodiment, methods of selecting maize plants with enhanced resistance to *Fusarium* ear mold are provided. In one aspect, a first maize plant is obtained that has at least one allele of a first marker locus and at least one allele of second marker locus. The first marker locus is located within an interval on chromosome 3 comprising and flanked by PHM12969 and PHM18211, and the second marker locus is located within an interval on chromosome 4 comprising and flanked by PHM10892 and PHM10262. The at least one allele of the first marker locus and the at least one allele of the second marker locus are eacg associated with enhanced resistance to *Fusarium* ear mold. The first maize plant can be crossed to a second maize plant, and the progeny plants resulting from the cross can be evaluated for the alleles of the first maize plant. Progeny plants that possess the alleles of the first maize plant can be selected as having enhanced resistance to *Fusarium* ear mold.

Maize plants identified and/or selected by any of the methods described herein are also of interest.

The plants can be in the "stiff stalk" heterotic group.

BRIEF DESCRIPTION OF FIGURES AND SEQUENCE LISTINGS

The invention can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. §1.822.

FIG. 1 shows the physical map arrangement of sequenced BACs (internally derived) on chromosome 3 that assemble to the region defined by and including PHM12969 (SEQ ID NO:1) and PHM18211 (SEQ ID NO:7). The positions of the PHM markers described herein are indicated.

FIG. 2 shows the physical map arrangement of sequenced BACs (internally derived) on chromosome 4 that assemble to the region defined by and including PHM10892 (SEQ ID NO:10) and PHM10262 (SEQ ID NO:22). The positions of the PHM markers described herein are indicated.

FIG. 3 shows an association analysis of a stiff stalk subpopulation, wherein chromosome 3 markers were tested for significance of association with *Fusarium* ear mold resistance. X axis: Distance expressed in cM on Chr. 3. Y axis: probability value. Markers on chromosome 3 that co-segregate with *Fusarium* ear mold resistance in the stiff stalk subpopulation at a p-level of ≤0.001 (the region defined by and including PHM12969 and PHM18211) are shown in the boxed region.

FIG. 4 shows an association analysis of a stiff stalk subpopulation, wherein chromosome 4 markers were tested for significance of association with *Fusarium* ear mold resistance. X axis: Distance expressed in cM on Chr. 4. Y axis: probability value. Markers on chromosome 4 that co-segregate with *Fusarium* ear mold resistance in the stiff stalk subpopulation at a p-level of ≤0.001 (the region defined by and including PHM10892 and PHM10262) are shown in the boxed region.

FIG. 5 shows the FUSERS scale used as a guide to score *Fusarium* ear mold infection.

SEQ ID NO:1 is the reference sequence for PHM12969.
SEQ ID NO:2 is the reference sequence for PHM2204.
SEQ ID NO:3 is the reference sequence for PHM9905.
SEQ ID NO:4 is the reference sequence for PHM12209.
SEQ ID NO:5 is the reference sequence for PHM13926.
SEQ ID NO:6 is the reference sequence for PHM10091.
SEQ ID NO:7 is the reference sequence for PHM18211.
SEQ ID NO:8 is the reference sequence for PHM1695.
SEQ ID NO:9 is the reference sequence for PHM939.
SEQ ID NO:10 is the reference sequence for PHM10892.
SEQ ID NO:11 is the reference sequence for PHM5273.
SEQ ID NO:12 is the reference sequence for PHM497.
SEQ ID NO:13 is the reference sequence for PHM4483.
SEQ ID NO:14 is the reference sequence for PHM2015.
SEQ ID NO:15 is the reference sequence for PHM10326.
SEQ ID NO:16 is the reference sequence for PHM9363.
SEQ ID NO:17 is the reference sequence for PHM18162.
SEQ ID NO:18 is the reference sequence for PHM9942.
SEQ ID NO:19 is the reference sequence for PHM5247.
SEQ ID NO:20 is the reference sequence for PHM3985.
SEQ ID NO:21 is the reference sequence for PHM6226.
SEQ ID NO:22 is the reference sequence for PHM10262.
SEQ ID NO:23 is the external forward primer for PHM12969.
SEQ ID NO:24 is the internal forward primer for PHM12969.
SEQ ID NO:25 is the internal reverse primer for PHM12969.
SEQ ID NO:26 is the external reverse primer for PHM12969.
SEQ ID NO:27 is the external forward primer for PHM2204.
SEQ ID NO:28 is the internal forward primer for PHM2204.
SEQ ID NO:29 is the internal reverse primer for PHM2204.
SEQ ID NO:30 is the external reverse primer for PHM2204.
SEQ ID NO:31 is the external forward primer for PHM9905.
SEQ ID NO:32 is the internal forward primer for PHM9905.
SEQ ID NO:33 is the internal reverse primer for PHM9905.
SEQ ID NO:34 is the external reverse primer for PHM9905.
SEQ ID NO:35 is the external forward primer for PHM12209.
SEQ ID NO:36 is the internal forward primer for PHM12209.
SEQ ID NO:37 is the internal reverse primer for PHM12209.
SEQ ID NO:38 is the external reverse primer for PHM12209.
SEQ ID NO:39 is the external forward primer for PHM13926.
SEQ ID NO:40 is the internal forward primer for PHM13926.
SEQ ID NO:41 is the internal reverse primer for PHM13926.
SEQ ID NO:42 is the external reverse primer for PHM13926.
SEQ ID NO:43 is the external forward primer for PHM10091.
SEQ ID NO:44 is the internal forward primer for PHM10091.
SEQ ID NO:45 is the internal reverse primer for PHM10091.
SEQ ID NO:46 is the external reverse primer for PHM10091.
SEQ ID NO:47 is the external forward primer for PHM18211.
SEQ ID NO:48 is the internal forward primer for PHM18211.
SEQ ID NO:49 is the internal reverse primer for PHM18211.
SEQ ID NO:50 is the external reverse primer for PHM18211.
SEQ ID NO:51 is the external forward primer for PHM1695.
SEQ ID NO:52 is the internal forward primer for PHM1695.

SEQ ID NO:53 is the internal reverse primer for PHM1695.
SEQ ID NO:54 is the external reverse primer for PHM1695.
SEQ ID NO:55 is the external forward primer for PHM939.
SEQ ID NO:56 is the internal forward primer for PHM939.
SEQ ID NO:57 is the internal reverse primer for PHM939.
SEQ ID NO:58 is the external reverse primer for PHM939.
SEQ ID NO:59 is the external forward primer for PHM10892.
SEQ ID NO:60 is the internal forward primer for PHM10892.
SEQ ID NO:61 is the internal reverse primer for PHM10892.
SEQ ID NO:62 is the external reverse primer for PHM10892.
SEQ ID NO:63 is the external forward primer for PHM5273.
SEQ ID NO:64 is the internal forward primer for PHM5273.
SEQ ID NO:65 is the internal reverse primer for PHM5273.
SEQ ID NO:66 is the external reverse primer for PHM5273.
SEQ ID NO:67 is the external forward primer for PHM497.
SEQ ID NO:68 is the internal forward primer for PHM497.
SEQ ID NO:69 is the internal reverse primer for PHM497.
SEQ ID NO:70 is the external reverse primer for PHM497.
SEQ ID NO:71 is the external forward primer for PHM4483.
SEQ ID NO:72 is the internal forward primer for PHM4483.
SEQ ID NO:73 is the internal reverse primer for PHM4483.
SEQ ID NO:74 is the external reverse primer for PHM4483.
SEQ ID NO:75 is the external forward primer for PHM2015.
SEQ ID NO:76 is the internal forward primer for PHM2015.
SEQ ID NO:77 is the internal reverse primer for PHM2015.
SEQ ID NO:78 is the external reverse primer for PHM2015.
SEQ ID NO:79 is the external forward primer for PHM10326.
SEQ ID NO:80 is the internal forward primer for PHM10326.
SEQ ID NO:81 is the internal reverse primer for PHM10326.
SEQ ID NO:82 is the external reverse primer for PHM10326.
SEQ ID NO:83 is the external forward primer for PHM9363.
SEQ ID NO:84 is the internal forward primer for PHM9363.
SEQ ID NO:85 is the internal reverse primer for PHM9363.
SEQ ID NO:86 is the external reverse primer for PHM9363.
SEQ ID NO:87 is the external forward primer for PHM18162.
SEQ ID NO:88 is the internal forward primer for PHM18162.
SEQ ID NO:89 is the internal reverse primer for PHM18162.
SEQ ID NO:90 is the external reverse primer for PHM18162.
SEQ ID NO:91 is the external forward primer for PHM9942.
SEQ ID NO:92 is the internal forward primer for PHM9942.
SEQ ID NO:93 is the internal reverse primer for PHM9942.
SEQ ID NO:94 is the external reverse primer for PHM9942.
SEQ ID NO:95 is the external forward primer for PHM5247.
SEQ ID NO:96 is the internal forward primer for PHM5247.
SEQ ID NO:97 is the internal reverse primer for PHM5247.
SEQ ID NO:98 is the external reverse primer for PHM5247.
SEQ ID NO:99 is the external forward primer for PHM3985.
SEQ ID NO:100 is the internal forward primer for PHM3985.
SEQ ID NO:101 is the internal reverse primer for PHM3985.
SEQ ID NO:102 is the external reverse primer for PHM3985.
SEQ ID NO:103 is the external forward primer for PHM6226.
SEQ ID NO:104 is the internal forward primer for PHM6226.
SEQ ID NO:105 is the internal reverse primer for PHM6226.
SEQ ID NO:106 is the external reverse primer for PHM6226.
SEQ ID NO:107 is the external forward primer for PHM10262.
SEQ ID NO:108 is the internal forward primer for PHM10262.
SEQ ID NO:109 is the internal reverse primer for PHM10262.
SEQ ID NO:110 is the external reverse primer for PHM10262.
SEQ ID NO:111 is primer 1 of marker PHM12209-20-U.
SEQ ID NO:112 is primer 2 of marker PHM12209-20-U.
SEQ ID NO:113 is probe 1 of marker PHM12209-20-U.
SEQ ID NO:114 is probe 2 of marker PHM12209-20-U.
SEQ ID NO:115 is primer 1 of marker PHM12209-21-U.
SEQ ID NO:116 is primer 2 of marker PHM12209-21-U.
SEQ ID NO:117 is probe 1 of marker PHM12209-21-U.
SEQ ID NO:118 is probe 2 of marker PHM12209-21-U.
SEQ ID NO:119 is primer 1 of marker PHM12209-23-U.
SEQ ID NO:120 is primer 2 of marker PHM12209-23-U.
SEQ ID NO:121 is probe 1 of marker PHM12209-23-U.
SEQ ID NO:122 is probe 2 of marker PHM12209-23-U.
SEQ ID NO:123 is primer 1 of marker PHM10892-3-U.
SEQ ID NO:124 is primer 2 of marker PHM10892-3-U.
SEQ ID NO:125 is probe 1 of marker PHM10892-3-U.
SEQ ID NO:126 is probe 2 of marker PHM10892-3-U.

DETAILED DESCRIPTION

The present invention provides allelic compositions in maize and methods for identifying and selecting maize plants with enhanced resistance to *Fusarium* ear mold. The following definitions are provided as an aid to understand this invention.

Before describing the present invention in detail, it is to be understood that this invention is not limited to particular embodiments, which can, of course, vary. It is also to be understood that the terminology used herein is for the purpose of describing particular embodiments only, and is not intended to be limiting. As used in this specification and the appended claims, terms in the singular and the singular forms "a", "an" and "the", for example, include plural referents unless the content clearly dictates otherwise. Thus, for example, reference to "plant", "the plant" or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Unless otherwise indicated, nucleic acids are written left to right in 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

The term "allele" refers to one of two or more different nucleotide sequences that occur at a specific locus.

An "amplicon" is an amplified nucleic acid, e.g., a nucleic acid that is produced by amplifying a template nucleic acid by any available amplification method (e.g., PCR, LCR, transcription, or the like).

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods.

The term "assemble" applies to BACs and their propensities for coming together to form contiguous stretches of DNA. A BAC "assembles" to a contig based on sequence alignment, if the BAC is sequenced, or via the alignment of its BAC fingerprint to the fingerprints of other BACs. The assemblies can be found using the Maize Genome Browser, which is publicly available on the internet.

An allele is "associated with" a trait when it is part of or linked to a DNA sequence or allele that affects the expression of a trait. The presence of the allele is an indicator of how the trait will be expressed.

A "BAC", or bacterial artificial chromosome, is a cloning vector derived from the naturally occurring F factor of *Escherichia coli*. BACs can accept large inserts of DNA sequence. In maize, a number of BACs, or bacterial artificial chromosomes, each containing a large insert of maize genomic DNA, have been assembled into contigs (overlapping contiguous genetic fragments, or "contiguous DNA").

"Backcrossing" refers to the process whereby hybrid progeny are repeatedly crossed back to one of the parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. (1995) Marker-assisted backcrossing: a practical example, in Techniques et Utilisations des Marqueurs Moleculaires Les Colloques, Vol. 72, pp. 45-56, and Openshaw et al., (1994) Marker-assisted Selection in Backcross Breeding, Analysis of Molecular Marker Data, pp. 41-43. The initial cross gives rise to the F1 generation; the term "BC1" then refers to the second use of the recurrent parent, "BC2" refers to the third use of the recurrent parent, and so on.

A centimorgan ("cM") is a unit of measure of recombination frequency. One cM is equal to a 1% chance that a marker at one genetic locus will be separated from a marker at a second locus due to crossing over in a single generation.

As used herein, the term "chromosomal interval" designates a contiguous linear span of genomic DNA that resides in planta on a single chromosome. The genetic elements or genes located on a single chromosomal interval are physically linked. The size of a chromosomal interval is not particularly limited. In some aspects, the genetic elements located within a single chromosomal interval are genetically linked, typically with a genetic recombination distance of, for example, less than or equal to 20 cM, or alternatively, less than or equal to 10 cM. That is, two genetic elements within a single chromosomal interval undergo recombination at a frequency of less than or equal to 20% or 10%.

A "chromosome" can also be referred to as a "linkage group".

The term "complement" refers to a nucleotide sequence that is complementary to a given nucleotide sequence, i.e. the sequences are related by the base-pairing rules.

The term "contiguous DNA" refers to overlapping contiguous genetic fragments.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

A "diploid" organism (such as a plant) has two sets (genomes) of chromosomes.

"Disease resistance" is a characteristic of a plant, wherein the plant avoids the disease symptoms that are the outcome of plant-pathogen interactions, such as interactions between maize and the *fusarium* species *F. verticillioides, F. proliferatum*, and/or *F. subglutinans*. That is, pathogens are prevented from causing plant diseases and the associated disease symptoms, or alternatively, the disease symptoms caused by the pathogen are minimized or lessened. One of skill in the art will appreciate that the compositions and methods disclosed herein can be used with other compositions and methods available in the art for protecting plants from pathogen attack.

A "doubled haploid" is developed by doubling the haploid set of chromosomes. A doubled haploid plant is considered a homozygous plant.

An "elite line" is any line that has resulted from breeding and selection for superior agronomic performance.

"Enhanced resistance" refers to an increased level of resistance against a particular pathogen, a wide spectrum of pathogens, or an infection caused by the pathogen(s). An increased level of resistance against the fungal pathogens *Fusarium verticillioides* (Fv), *Fusarium proliferatum* (Fp), and

*Fusarium subglutinans* (Fs), for example, constitutes "enhanced" or improved fungal resistance. The embodiments of the invention will enhance or improve fungal plant pathogen resistance, such that the resistance of the plant to a fungal pathogen or pathogens will increase, which in turn, will increase resistance to the disease caused by the fungal pathogen. The term "enhance" refers to improve, increase, amplify, multiply, elevate, raise, and the like. Herein, plants of the invention are described as having "enhanced resistance" to the *Fusarium* species *F. verticillioides, F. proliferatum*, and *F. subglutinans* and/or the ear mold caused by these pathogens, as a result of specific alleles at the locus of the invention.

*F. verticillioides, F. proliferatum*, and *F. subglutinans* are the fungal pathogens that induce *Fusarium* ear mold (or ear rot) in maize. The fungal pathogens are also referred to collectively herein as *Fusarium.*

A "favorable allele" is the allele at a particular locus that confers, or contributes to, an agronomically desirable phenotype, e.g., enhanced resistance to *Fusarium* ear mold. A favorable allele of a marker is a marker allele that segregates with the favorable phenotype.

"Fragment" is intended to mean a portion of a nucleotide sequence. Fragments can be used as hybridization probes or PCR primers using methods disclosed herein.

As used herein, "fungal resistance" refers to enhanced resistance or tolerance to a fungal pathogen when compared to that of a wild type plant. Effects may vary from a slight increase in tolerance to the effects of the fungal pathogen (e.g., partial inhibition) to total resistance such that the plant is unaffected by the presence of the fungal pathogen.

"*Fusarium* ear mold", sometimes referred to as *Fusarium* ear rot, is the disease caused by species of the *Gibberella fuijkuroi* complex, namely *F. verticillioides, F. proliferatum*, and/or *F. subglutinans.*

A "genetic map" is a description of genetic linkage relationships among loci on one or more chromosomes (or linkage groups) within a given species, generally depicted in a diagrammatic or tabular form. For each genetic map, distances between loci are measured by how frequently their alleles appear together in a population (i.e. their recombination frequencies). Alleles can be detected using DNA or protein markers, or observable phenotypes. A genetic map is a product of the mapping population, types of markers used, and the polymorphic potential of each marker between different populations. Genetic distances between loci can differ from one genetic map to another. However, information can be correlated from one map to another using common markers. One of ordinary skill in the art can use common marker positions to identify the positions of markers and other loci of interest on each individual genetic map. The order of loci should not change between maps, although frequently there are small changes in marker orders due to e.g. markers detecting alternate duplicate loci in different populations, differences in statistical approaches used to order the markers, novel mutation or laboratory error.

The term "Genetic Marker" shall refer to any type of nucleic acid based marker, including but not limited to, Restriction Fragment Length Polymorphism (RFLP), Simple Sequence Repeat (SSR), Random Amplified Polymorphic DNA (RAPD), Cleaved Amplified Polymorphic Sequences (CAPS) (Rafalski and Tingey, 1993, *Trends in Genetics* 9:275-280), Amplified Fragment Length Polymorphism (AFLP) (Vos et al, 1995, *Nucleic Acids Res.* 23:4407-4414), Single Nucleotide Polymorphism (SNP) (Brookes, 1999, *Gene* 234:177-186), Sequence Characterized Amplified Region (SCAR) (Paran and Michelmore, 1993, *Theor. Appl. Genet.* 85:985-993), Sequence Tagged Site (STS) (Onozaki et al., 2004, *Euphytica* 138:255-262), Single Stranded Conformation Polymorphism (SSCP) (Orita et al., 1989, *Proc Natl Acad Sci USA* 86:2766-2770), Inter-Simple Sequence Repeat (ISSR) (Blair et al., 1999, *Theor. Appl. Genet.* 98:780-792), Inter-Retrotransposon Amplified Polymorphism (IRAP), Retrotransposon-Microsatellite Amplified Polymorphism (REMAP) (Kalendar et al., 1999, *Theor. Appl. Genet.* 98:704-711), an RNA cleavage product (such as a Lynx tag), and the like.

"Genetic recombination frequency" is the frequency of a crossing over event (recombination) between two genetic loci. Recombination frequency can be observed by following the segregation of markers and/or traits following meiosis.

"Genome" refers to the total DNA, or the entire set of genes, carried by a chromosome or chromosome set.

The term "genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells that can be cultured into a whole plant.

A plant referred to as "haploid" has a single set (genome) of chromosomes.

A "haplotype" is the genotype of an individual at a plurality of genetic loci, i.e. a combination of alleles. Typically, the genetic loci described by a haplotype are physically and genetically linked, i.e., on the same chromosome segment. The term "haplotype" can refer to polymorphisms at a particular locus, such as a single marker locus, or polymorphisms at multiple loci along a chromosomal segment. Herein, a "favorable haplotype" is one associated with a higher *Fusarium* ear mold resistance score, meaning that a plant having that haplotype has fewer symptoms. An "unfavorable haplotype" is one associated with a reduction in the *Fusarium* ear mold resistance score. Scores can be obtained, for example, using the scale in FIG. 5.

A "heterotic group" comprises a set of genotypes that perform well when crossed with genotypes from a different heterotic group (Hallauer et al. (1998) Corn breeding, p. 463-564. In G. F. Sprague and J. W. Dudley (ed.) *Corn and corn improvement*). Inbred lines are classified into heterotic groups, and are further subdivided into families within a heterotic group, based on several criteria such as pedigree, molecular marker-based associations, and performance in hybrid combinations (Smith et al. (1990) *Theor. Appl. Gen.* 80:833-840). The two most widely used heterotic groups in the United States are referred to as "Iowa Stiff Stalk Synthetic" (also referred to herein as "stiff stalk") and "Lancaster" or "Lancaster Sure Crop" (sometimes referred to as NSS, or non-Stiff Stalk).

The term "heterozygous" means a genetic condition wherein different alleles reside at corresponding loci on homologous chromosomes.

The term "homozygous" means a genetic condition wherein identical alleles reside at corresponding loci on homologous chromosomes.

The term "hybrid" refers to the progeny obtained between the crossing of at least two genetically dissimilar parents.

"Hybridization" or "nucleic acid hybridization" refers to the pairing of complementary RNA and DNA strands as well as the pairing of complementary DNA single strands.

The term "hybridize" means to form base pairs between complementary regions of nucleic acid strands.

An "IBM genetic map" can refer to any of the following maps: IBM, IBM2, IBM2 neighbors, IBM2 FPC0507, IBM2 2004 neighbors, IBM2 2005 neighbors, IBM2 2005 neighbors frame, IBM2 2008 neighbors, IBM2 2008 neighbors frame, or the latest version on the maizeGDB website. IBM genetic maps are based on a B73×Mo17 population in which the progeny from the initial cross were random-mated for multiple generations prior to constructing recombinant inbred lines for mapping. Newer versions reflect the addition of genetic and BAC mapped loci as well as enhanced map refinement due to the incorporation of information obtained from other genetic or physical maps, cleaned data, or the use of new algorithms.

The term "inbred" refers to a line that has been bred for genetic homogeneity.

The term "indel" refers to an insertion or deletion, wherein one line may be referred to as having an insertion relative to a second line, or the second line may be referred to as having a deletion relative to the first line.

The term "introgression" or "introgressing" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background. For example, the chromosome 3 locus and/or the chromosome 4 locus described herein may be introgressed into a recurrent parent that is not resistant or only partially resistant to the *Fusarium* species that cause ear mold and/or the ear mold itself. The recurrent parent line with the introgressed gene (s) or locus (loci) then has enhanced resistance to the *Fusarium* species that cause ear mold and/or the ear mold itself.

The process of "introgressing" is often referred to as "backcrossing" when the process is repeated two or more times.

As used herein, the term "linkage" is used to describe the degree with which one marker locus is associated with another marker locus or some other locus (for example, a *Fusarium* ear mold resistance locus). The linkage relationship between a molecular marker and a locus affecting a phenotype is given as a "probability" or "adjusted probability". Linkage can be expressed as a desired limit or range. For example, in some embodiments, any marker is linked (genetically and physically) to any other marker when the markers are separated by less than 50, 40, 30, 25, 20, or 15 map units (or cM) of a single meiosis map (a genetic map based on a population that has undergone one round of meiosis (e.g. an $F_2$)). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same chromosome.) As used herein, linkage can be between two markers, or alternatively between a marker and a phenotype. A marker locus can be "associated with" (linked to) a trait, e.g., *Fusarium* ear mold resistance. The degree of linkage of a molecular marker to a phenotypic trait is measured, e.g., as a statistical probability of co-segregation of that molecular marker with the phenotype.

Linkage disequilibrium is most commonly assessed using the measure $r^2$, which is calculated using the formula described by Hill, W. G. and Robertson, A, *Theor. Appl. Genet.* 38:226-231 (1968). When $r^2=1$, complete LD exists between the two marker loci, meaning that the markers have not been separated by recombination and have the same allele frequency. Values for $r^2$ above ⅓ indicate sufficiently strong LD to be useful for mapping (Ardlie et al., *Nature Reviews Genetics* 3:299-309 (2002)). Hence, alleles are in linkage disequilibrium when $r^2$ values between pairwise marker loci are greater than or equal to 0.33, 0.4, 0.5, 0.6, 0.7, 0.8, 0.9, or 1.0.

As used herein, "linkage equilibrium" describes a situation where two markers independently segregate, i.e., sort among progeny randomly. Markers that show linkage equilibrium are considered unlinked (whether or not they lie on the same chromosome).

A "locus" is a position on a chromosome where a nucleotide, gene, sequence, or marker is located.

The "logarithm of odds (LOD) value" or "LOD score" (Risch, Science 255:803-804 (1992)) is used in interval mapping to describe the degree of linkage between two marker loci. A LOD score of three between two markers indicates that linkage is 1000 times more likely than no linkage, while a LOD score of two indicates that linkage is 100 times more likely than no linkage. LOD scores greater than or equal to two may be used to detect linkage.

"Maize" refers to a plant of the *Zea mays* L. ssp. mays and is also known as "corn".

The term "maize plant" includes: whole maize plants, maize plant cells, maize plant protoplast, maize plant cell or maize tissue cultures from which maize plants can be regenerated, maize plant calli, and maize plant cells that are intact in maize plants or parts of maize plants, such as maize seeds, maize cobs, maize flowers, maize cotyledons, maize leaves, maize stems, maize buds, maize roots, maize root tips, and the like.

A "marker" is a nucleotide sequence or encoded product thereof (e.g., a protein) used as a point of reference. For markers to be useful at detecting recombinations, they need to detect differences, or polymorphisms, within the population being monitored. For molecular markers, this means differences at the DNA level due to polynucleotide sequence differences (e.g. SSRs, RFLPs, FLPs, SNPs). The genomic variability can be of any origin, for example, insertions, deletions, duplications, repetitive elements, point mutations, recombination events, or the presence and sequence of transposable elements. A marker can be derived from genomic nucleotide sequence or from expressed nucleic acids (e.g., ESTs) and can also refer to nucleic acids used as probes or primer pairs capable of amplifying sequence fragments via the use of PCR-based methods. A large number of maize molecular markers are known in the art, and are published or available from various sources, such as the Maize GDB internet resource and the Arizona Genomics Institute internet resource run by the University of Arizona.

Markers corresponding to genetic polymorphisms between members of a population can be detected by methods well-established in the art. These include, e.g., DNA sequencing, PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also known for the detection of expressed sequence tags (ESTs) and SSR markers derived from EST sequences and randomly amplified polymorphic DNA (RAPD).

A "marker allele", alternatively an "allele of a marker locus", can refer to one of a plurality of polymorphic nucleotide sequences found at a marker locus in a population that is polymorphic for the marker locus.

"Marker assisted selection" (of MAS) is a process by which phenotypes are selected based on marker genotypes.

"Marker assisted counter-selection" is a process by which marker genotypes are used to identify plants that will not be selected, allowing them to be removed from a breeding program or planting.

A "marker haplotype" refers to a combination of alleles at a marker locus.

A "marker locus" is a specific chromosome location in the genome of a species where a specific marker can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

A "marker probe" is a nucleic acid sequence or molecule that can be used to identify the presence of a marker locus, e.g., a nucleic acid probe that is complementary to a marker locus sequence, through nucleic acid hybridization. Marker probes comprising 30 or more contiguous nucleotides of the marker locus ("all or a portion" of the marker locus sequence) may be used for nucleic acid hybridization. Alternatively, in some aspects, a marker probe refers to a probe of any type that is able to distinguish (i.e., genotype) the particular allele that is present at a marker locus.

"Nucleotide sequence", "polynucleotide", "nucleic acid sequence", and "nucleic acid fragment" are used interchangeably and refer to a polymer of RNA or DNA that is single- or double-stranded, optionally containing synthetic, non-natural or altered nucleotide bases. A "nucleotide" is a monomeric unit from which DNA or RNA polymers are constructed, and consists of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "phenotype", or "phenotypic trait" or "trait" refers to one or more traits of an organism. The phenotype can be observable to the naked eye, or by any other means of evaluation known in the art, e.g., microscopy, biochemical analysis, or an electromechanical assay. In some cases, a phenotype is directly controlled by a single gene or genetic locus, i.e., a "single gene trait". In other cases, a phenotype is the result of several genes.

Each marker with a "PHM" designation followed by a number (and no extensions) represents two sets of primers (external and internal) that when used in a nested PCR, amplify a specific piece of DNA. The external set is used in the first round of PCR, after which the internal sequences are used for a second round of PCR on the products of the first round. This increases the specificity of the reaction. The annealing temperature for the PHM markers (consisting of two sets of primers) is 55° C.

A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination.

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant.

A "polymorphism" is a variation in the DNA that is too common to be due merely to new mutation. A polymorphism must have a frequency of at least 1% in a population. A polymorphism can be a single nucleotide polymorphism, or SNP, or an insertion/deletion polymorphism, also referred to herein as an "indel".

The "probability value" or "p-value" is the statistical likelihood that the particular combination of a phenotype and the presence or absence of a particular marker allele is random. Thus, the lower the probability score, the greater the likelihood that a phenotype and a particular marker will co-segregate. In some aspects, the probability score is considered "significant" or "nonsignificant". In some embodiments, a probability score of 0.05 (p=0.05, or a 5% probability) of random assortment is considered a significant indication of co-segregation. However, an acceptable probability can be any probability of less than 50% (p=0.5). For example, a significant probability can be less than 0.25, less than 0.20, less than 0.15, less than 0.1, less than 0.05, less than 0.01, or less than 0.001.

The term "progeny" refers to the offspring generated from a cross.

A "progeny plant" is generated from a cross between two plants.

A "production marker" or "production SNP marker" is a marker that has been developed for high-throughput purposes. Production SNP markers are developed to detect specific polymorphisms and are designed for use with a variety of chemistries and platforms. The marker names used here begin with a PHM prefix to denote 'Pioneer Hybrid Marker', followed by a number that is specific to the sequence from which it was designed, followed by a "." or a "-" and then a suffix that is specific to the DNA polymorphism. A marker version can also follow (A, B, C etc) that denotes the version of the marker designed to that specific polymorphism.

The term "quantitative trait locus" or "QTL" refers to a region of DNA that is associated with the differential expression of a phenotypic trait in at least one genetic background, e.g., in at least one breeding population. QTLs are closely linked to the gene or genes that underlie the trait in question.

A "reference sequence" is a defined sequence used as a basis for sequence comparison. The reference sequence is obtained by genotyping a number of lines at the locus, aligning the nucleotide sequences in a sequence alignment program (e.g. Sequencher), and then obtaining the consensus sequence of the alignment.

A "topcross test" is a progeny test derived by crossing each parent with the same tester, usually a homozygous line. The parent being tested can be an open-pollinated variety, a cross, or an inbred line.

The phrase "under stringent conditions" refers to conditions under which a probe or polynucleotide will hybridize to a specific nucleic acid sequence, typically in a complex mixture of nucleic acids, but to essentially no other sequences. Stringent conditions are sequence-dependent and will be different in different circumstances.

Longer sequences hybridize specifically at higher temperatures. Generally, stringent conditions are selected to be about 5-10° C. lower than the thermal melting point (Tm) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3, and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions are often: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C., depending on primer length. Additional guidelines for determining hybridization parameters are provided in numerous references.

An "unfavorable allele" of a marker is a marker allele that segregates with the unfavorable plant phenotype, therefore providing the benefit of identifying plants that can be removed from a breeding program or planting.

Sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp, CABIOS. 5:151 153 (1989)) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Press: Cold Spring Harbor, 1989 (hereinafter "Sambrook").

Before describing the present invention in detail, it should be understood that this invention is not limited to particular embodiments. It also should be understood that the terminology used herein is for the purpose of describing particular embodiments, and is not intended to be limiting. As used herein and in the appended claims, terms in the singular and the singular forms "a", "an" and "the", for example, include plural referents unless the content clearly dictates otherwise. Thus, for example, reference to "plant", "the plant" or "a plant" also includes a plurality of plants. Depending on the context, use of the term "plant" can also include genetically similar or identical progeny of that plant. The use of the term "a nucleic acid" optionally includes many copies of that nucleic acid molecule. Turning now to the embodiments:

*Fusarium* Ear Mold Resistance

*Fusarium* ear mold (also referred to as *Fusarium* ear rot) is a devastating disease of maize caused by species of the *Gibberella fuijkuroi* complex, namely *F. verticillioides, F. proliferatum*, and/or *F. subglutinans*. The identification of molecular markers and alleles of molecular markers that are associated with *Fusarium* ear mold resistance allows selection for resistance based solely on the genetic composition of the progeny. Methods for identifying and selecting maize plants with enhanced resistance to *Fusarium* ear mold through the evaluation of genetic composition (as assessed using molecular markers and their alleles) are presented herein.

Genetic Mapping

It has been recognized for quite some time that specific genetic loci correlating with particular phenotypes, such as resistance to *Fusarium* ear mold, can be mapped in an organism's genome. The plant breeder can advantageously use molecular markers to identify desired individuals by detecting marker alleles that show a statistically significant probability of co-segregation with a desired phenotype, manifested as linkage disequilibrium. By identifying a molecular marker or clusters of molecular markers that co-segregate with a trait of interest, the breeder is able to rapidly select a desired phenotype by selecting for the proper molecular marker allele (a process called marker-assisted selection, or MAS). Such markers could also be used by breeders to design genotypes in silico and to practice whole genome selection.

A variety of methods well known in the art are available for detecting molecular markers or clusters of molecular markers that co-segregate with a trait of interest, such as resistance to *Fusarium* ear mold. The basic idea underlying these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference.

Two such methods used to detect trait loci of interest are: 1) Population-based association analysis and 2) Traditional linkage analysis. In a population-based association analysis, lines are obtained from pre-existing populations with multiple founders, e.g. elite breeding lines. Population-based association analyses rely on the decay of linkage disequilibrium (LD) and the idea that in an unstructured population, only correlations between genes controlling a trait of interest and markers closely linked to those genes will remain after so many generations of random mating. In reality, most pre-existing populations have population substructure. Thus, the use of a structured association approach helps to control population structure by allocating individuals to populations using data obtained from markers randomly distributed across the genome, thereby minimizing disequilibrium due to population structure within the individual populations (also called subpopulations). The phenotypic values are compared to the genotypes (alleles) at each marker locus for each line in the subpopulation. A significant marker-trait association indicates the close proximity between the marker locus and one or more genetic loci that are involved in the expression of that trait.

The same principles underlie traditional linkage analysis; however, LD is generated by creating a population from a small number of founders. The founders are selected to maximize the level of polymorphism within the constructed population, and polymorphic sites are assessed for their level of cosegregation with a given phenotype. A number of statistical methods have been used to identify significant marker-trait associations. One such method is an interval mapping approach (Lander and Botstein, *Genetics* 121:185-199 (1989), in which each of many positions along a genetic map (say at 1 cM intervals) is tested for the likelihood that a gene controlling a trait of interest is located at that position. The genotype/phenotype data are used to calculate for each test position a LOD score (log of likelihood ratio). When the LOD score exceeds a threshold value, there is significant evidence for the location of a gene controlling the trait of interest at that position on the genetic map (which will fall between two particular marker loci).

The present invention provides maize marker loci that demonstrate statistically significant co-segregation with resistance to *Fusarium* ear mold, as determined by association analysis. Detection of these loci or additional linked loci can be used in marker assisted maize breeding programs to produce plants with enhanced resistance to *Fusarium* ear mold.

Marker Compositions

Markers associated with resistance to *Fusarium* ear mold in maize are identified herein, and methods involve detecting the presence of one or more marker alleles associated with the enhanced resistance in the germplasm of a maize plant. The maize plant can be a hybrid or inbred and may be in the stiff stalk heterotic group.

For the QTL identified on chromosome 3, the marker locus can be selected from any of the marker loci provided in TABLE 1, including PHM12969, PHM1695, PHM12209, PHM2204, PHM9905, PHM13926, PHM10091, and PHM18211; any of the SNP marker loci provided in TABLE 5, including a "C" at PHM12209.11, a "T" at PHM12209.20, a "C" at PHM12209.21, a "G" at PHM12209.22, a "C" at PHM12209.23, an "A" at PHM9905.11, a "T" at PHM9905.13, a "G" at PHM9905.35, a "T" at PHM2204.88, an "A" at PHM2204.105, a "C" at PHM13926.25, a "G" at PHM13926.27, a "G" at PHM13926.28, and a "G" at PHM13926.32, as well as any other marker linked to these markers (linked markers can be determined from the MaizeGDB resource).

For the QTL identified on chromosome 4, the marker locus can be selected from any of the marker loci provided in TABLE 2, including PHM2015, PHM10326, PHM497, PHM4483, PHM5273, PHM939, PHM10892, PHM9363, PHM18162, PHM9942, PHM5247, PHM3985, PHM6226, and PHM10262; any of the SNP marker loci provided in TABLE 6, including a "C" at PHM10892.3, a "G" at PHM939.47, and an "A" at PHM939.48; as well as any other marker linked to these markers (linked markers can be determined from the MaizeGDB resource).

Physical Map Locations of QTLs

The genetic elements or genes located on a contiguous linear span of genomic DNA on a single chromosome are physically linked.

For the QTL on chromosome 3, the two markers with the largest physical distance between them that still remain associated with the phenotype of interest, *Fusarium* ear mold resistance, are PHM12969 and PHM18211. PHM12969 is located on BACs c0437d18, c0094g18, and b0219j14. PHM18211 is located on BACs c0482d19 and c0060e22. These two BAC regions delineate the *Fusarium* ear mold resistance QTL on the maize physical map (FIG. 1). Any polynucleotide that assembles to the contiguous DNA between and including SEQ ID NO:1 (the reference sequence for PHM12969), or a nucleotide sequence that is 95% identical to SEQ ID NO:1 based on the Clustal V method of alignment, and SEQ ID NO:7 (the reference sequence for PHM18211), or a nucleotide sequence that is 95% identical to SEQ ID NO:7 based on the Clustal V method of alignment, can house marker loci that are associated with the *Fusarium* ear mold resistance trait. FIG. 1 shows the physical map arrangement of the sequenced BACs that make up the contiguous stretch of DNA between and including PHM12969 and PHM18211.

For the QTL located on chromsome 4, the two markers with the largest physical distance between them that still remain associated with the phenotype of interest, *Fusarium* ear mold resistance, are PHM10892 and PHM10262. PHM10892 is located on BAC b0269h08, while PHM10262 is located on BACs c0237f22 and c0069i21. These two BAC regions delineate the *Fusarium* ear mold resistance QTL on the maize physical map (FIG. 2). Any polynucleotide that assembles to the contiguous DNA between and including SEQ ID NO:10 (the reference sequence for PHM10892), or a nucleotide sequence that is 95% identical to SEQ ID NO:10 based on the Clustal V method of alignment, and SEQ ID NO:22 (the reference sequence for PHM10262), or a nucleotide sequence that is 95% identical to SEQ ID NO:22 based on the Clustal V method of alignment, can house marker loci that are associated with the *Fusarium* ear mold resistance trait. FIG. 2 shows the physical map arrangement of the sequenced BACs that make up the contiguous stretch of DNA between and including PHM10892 and PHM10262.

Linkage Relationships

A common measure of linkage is the frequency with which traits cosegregate. This can be expressed as a percentage of cosegregation (recombination frequency) or in centiMorgans (cM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency.

Marker loci are themselves traits and can be assessed according to standard linkage analysis by tracking the marker loci during segregation. Thus, one cM is equal to a 1% chance that a marker locus will be separated from another locus, due to crossing over in a single generation.

The closer a marker is to a gene controlling a trait of interest, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are said to be "proximal to" each other.

Although particular marker alleles can show co-segregation with the *Fusarium* ear mold resistance phenotype, it is important to note that the marker locus is not necessarily responsible for the expression of the *Fusarium* ear mold resistance phenotype. For example, it is not a requirement that the marker polynucleotide sequence be part of a gene that imparts enhanced *Fusarium* ear mold resistance (for example, be part of the gene open reading frame). The association between a specific marker allele and the enhanced *Fusarium* ear mold resistance phenotype is due to the original "coupling" linkage phase between the marker allele and the allele in the ancestral maize line from which the allele originated. Eventually, with repeated recombination, crossing over events between the marker and genetic locus can change this orientation. For this reason, the favorable marker allele may change depending on the linkage phase that exists within the resistant parent used to create segregating populations. This does not change the fact that the marker can be used to monitor segregation of the phenotype. It only changes which marker allele is considered favorable in a given segregating population.

For the QTL on chromosome 3, markers identified in TABLES 1 and 5, as well as any marker within 50 cM of the markers identified in TABLES 1 and 5, can be used to predict *Fusarium* ear mold resistance in a maize plant. This includes any marker within 50 cM of the PHM markers, PHM12969, PHM1695, PHM12209, PHM2204, PHM9905, PHM13926, PHM10091, and PHM18211, and within 50 CM of the SNP markers, a "C" at PHM12209.11, a "T" at PHM12209.20, a "C" at PHM12209.21, a "G" at PHM12209.22, a "C" at PHM12209.23, an "A" at PHM9905.11, a "T" at PHM9905.13, a "G" at PHM9905.35, a "T" at PHM2204.88, an "A" at PHM2204.105, a "C" at PHM13926.25, a "G" at PHM13926.27, a "G" at PHM13926.28, and a "G" at PHM13926.32.

For the QTL on chromosome 4, markers identified in TABLES 2 and 6, as well as any marker within 50 cM of the markers identified in TABLES 2 and 6, can be used to predict *Fusarium* ear mold resistance in a maize plant. This includes any marker within 50 cM of the PHM markers, PHM2015, PHM10326, PHM497, PHM4483, PHM5273, PHM939, PHM10892, PHM9363, PHM18162, PHM9942, PHM5247, PHM3985, PHM6226, and PHM10262, and within 50 cM of the SNP markers, a "C" at PHM10892.3, a "G" at PHM939.47, and an "A" at PHM939.48.

Chromosomal Intervals

Chromosomal intervals that correlate with *Fusarium* ear mold resistance are provided. A variety of methods well known in the art are available for identifying chromosomal intervals. The boundaries of such chromosomal intervals are drawn to encompass markers that will be linked to one or more QTL. In other words, the chromosomal interval is drawn such that any marker that lies within that interval (including the terminal markers that define the boundaries of the interval) can be used as a marker for *Fusarium* ear mold resistance. Each interval comprises at least one QTL, and furthermore, may indeed comprise more than one QTL. Close proximity of multiple QTL in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identify the same QTL or two different QTL. Regardless, knowledge of how many QTL are in a particular interval is not necessary to make or practice the invention.

The intervals described below show a clustering of markers that co-segregate with *Fusarium* ear mold resistance. The clustering of markers occurs in relatively small domains on the chromosomes, indicating the presence of one or more QTL in those chromosome regions. The QTL interval was drawn to encompass markers that co-segregate with *Fusarium* ear mold resistance. Intervals are defined by the markers on their termini, where the interval encompasses markers that map within the interval as well as the markers that define the termini. An interval described by the terminal markers that define the endpoints of the interval will include the terminal markers and any marker localizing within that chromosomal domain, whether those markers are currently known or unknown.

For the QTL on chromosome 3, an interval may be defined by and includes markers PHM12969 and PHM18211. For the QTL on chromosome 4, an interval may be defined by and includes PHM10892 and PHM10262. Any marker located within these intervals can find use as a marker for *Fusarium* ear mold resistance.

Chromosomal intervals can also be defined by markers that are linked to (show linkage disequilibrium with) a QTL marker, and $r^2$ is a common measure of linkage disequilibrium (LD) in the context of association studies. If the $r^2$ value of LD between a chromosome 3 marker locus lying within the interval of PHM12969 and PHM18211 and another chromosome 3 marker locus in close proximity is greater than ⅓ (Ardlie et al., Nature Reviews Genetics 3:299-309 (2002)), the loci are in linkage disequilibrium with one another.

Marker Alleles and Haplotypic Combinations

A marker of the invention can also be a combination of alleles at one or more marker loci. The alleles described below could be used in combination to identify and select maize plants with enhanced *Fusarium* ear mold resistance.

Favorable SNP alleles (i.e., associated with enhanced *Fusarium* ear mold resistance) at the QTL on chromosome 3 have been identified herein and include: a "C" at PHM12209.11, a "T" at PHM12209.20, a "C" at PHM12209.21, a "G" at PHM12209.22, a "C" at PHM12209.23, an "A" at PHM9905.11, a "T" at PHM9905.13, a "G" at PHM9905.35, a "T" at PHM2204.88, an "A" at PHM2204.105, a "C" at PHM13926.25, a "G" at PHM13926.27, a "G" at PHM13926.28, and a "G" at PHM 13926.32.

Favorable SNP alleles (i.e., associated with enhanced *Fusarium* ear mold resistance) at the QTL on chromosome 4 have been identified herein and include: a "C" at PHM10892.3, a "G" at PHM939.47, and an "A" at PHM939.48.

The skilled artisan would expect that there might be additional polymorphic sites at marker loci in and around the chromosome 3 and 4 markers identified herein, wherein one or more polymorphic sites is in linkage disequilibrium (LD) with an allele at one or more of the polymorphic sites in the haplotype. Two particular alleles at different polymorphic sites are said to be in LD if the presence of the allele at one of the sites tends to predict the presence of the allele at the other site on the same chromosome (Stevens, *Mol. Diag.* 4:309-17 (1999)).

Marker Assisted Selection

Molecular markers can be used in a variety of plant breeding applications (e.g. see Staub et al. (1996) *Hortscience* 31: 729-741; Tanksley (1983) *Plant Molecular Biology Reporter.* 1: 3-8). One of the main areas of interest is to increase the efficiency of backcrossing and introgressing genes using marker-assisted selection (MAS). A molecular marker that demonstrates linkage with a locus affecting a desired phenotypic trait provides a useful tool for the selection of the trait in a plant population. This is particularly true where the phenotype is hard to assay, e.g. many disease resistance traits, or, occurs at a late stage in plant development, e.g. kernel characteristics. Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination cannot occur between the marker and the gene. Such a marker is called a 'perfect marker'.

When a gene is introgressed by MAS, it is not only the gene that is introduced but also the flanking regions (Gepts. (2002). *Crop Sci;* 42: 1780-1790). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite maize line. This is also sometimes referred to as "yield drag." The size of the flanking region can be decreased by additional backcrossing, although this is not always successful, as breeders do not have control over the size of the region or the recombination breakpoints (Young et al. (1998) *Genetics* 120:579-585). In classical breeding it is usually only by chance that recombinations are selected that contribute to a reduction in the size of the donor segment (Tanksley et al. (1989). *Biotechnology* 7: 257-264). Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene, based on a single meiosis map distance. Markers will allow unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers (See Tanksley et al., supra). When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

The availability of integrated linkage maps of the maize genome containing increasing densities of public maize markers has facilitated maize genetic mapping and MAS. See, e.g. the IBM2 Neighbors maps, which are available online on the MaizeGDB website.

The key components to the implementation of MAS are: (i) Defining the population within which the marker-trait association will be determined, which can be a segregating population, or a random or structured population; (ii) monitoring the segregation or association of polymorphic markers relative to the trait, and determining linkage or association using statistical methods; (iii) defining a set of desirable markers based on the results of the statistical analysis, and (iv) the use and/or extrapolation of this information to the current set of breeding germplasm to enable marker-based selection decisions to be made. The markers described in this disclosure, as well as other marker types such as SSRs and FLPs, can be used in marker assisted selection protocols.

SSRs can be defined as relatively short runs of tandemly repeated DNA with lengths of 6 bp or less (Tautz (1989) *Nucleic Acid Research* 17: 6463-6471; Wang et al. (1994)

*Theoretical and Applied Genetics,* 88:1-6) Polymorphisms arise due to variation in the number of repeat units, probably caused by slippage during DNA replication (Levinson and Gutman (1987) *Mol Biol Evol* 4: 203-221). The variation in repeat length may be detected by designing PCR primers to the conserved non-repetitive flanking regions (Weber and May (1989) *Am J Hum Genet.* 44:388-396). SSRs are highly suited to mapping and MAS as they are multi-allelic, codominant, reproducible and amenable to high throughput automation (Rafalski et al. (1996) Generating and using DNA markers in plants. In: *Non-mammalian genomic analysis: a practical guide.* Academic press. pp 75-135).

Various types of SSR markers can be generated, and SSR profiles from resistant lines can be obtained by gel electrophoresis of the amplification products. Scoring of marker genotype is based on the size of the amplified fragment. An SSR service for maize is available to the public on a contractual basis by DNA Landmarks in Saint-Jean-sur-Richelieu, Quebec, Canada.

Various types of FLP markers can also be generated. Most commonly, amplification primers are used to generate fragment length polymorphisms. Such FLP markers are in many ways similar to SSR markers, except that the region amplified by the primers is not typically a highly repetitive region. Still, the amplified region, or amplicon, will have sufficient variability among germplasm, often due to insertions or deletions, such that the fragments generated by the amplification primers can be distinguished among polymorphic individuals, and such indels are known to occur frequently in maize (Bhattramakki et al. (2002). *Plant Mol Biol* 48, 539-547; Rafalski (2002b), supra).

SNP markers detect single base pair nucleotide substitutions. Of all the molecular marker types, SNPs are the most abundant, thus having the potential to provide the highest genetic map resolution (Bhattramakki et al. 2002 *Plant Molecular Biology* 48:539-547). SNPs can be assayed at an even higher level of throughput than SSRs, in a so-called 'ultra-high-throughput' fashion, as they do not require large amounts of DNA and automation of the assay may be straight-forward. SNPs also have the promise of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in: Gut (2001) *Hum Mutat* 17 pp. 475-492; Shi (2001) *Clin Chem* 47, pp. 164-172; Kwok (2000) *Pharmacogenomics* 1, pp. 95-100; Bhattramakki and Rafalski (2001) Discovery and application of single nucleotide polymorphism markers in plants. In: R. J. Henry, Ed, *Plant Genotyping: The DNA Fingerprinting of Plants,* CABI Publishing, Wallingford. A wide range of commercially available technologies utilize these and other methods to interrogate SNPs including Masscode™ (Qiagen), Invader® (Third Wave Technologies), SnapShot® (Applied Biosystems), Taqman® (Applied Biosystems) and Beadarrays™ (Illumina).

A number of SNPs together within a sequence, or across linked sequences, can be used to describe a haplotype for any particular genotype (Ching et al. (2002), *BMC Genet.* 3:19 pp Gupta et al. 2001, Rafalski (2002b), *Plant Science* 162:329-333). Haplotypes can be more informative than single SNPs and can be more descriptive of any particular genotype. For example, a single SNP may be allele 'T' for a specific line or variety with resistance to *Fusarium* ear mold, but the allele 'T' might also occur in the maize breeding population being utilized for recurrent parents. In this case, a haplotype, e.g. a combination of alleles at linked SNP markers, may be more informative. Once a unique haplotype has been assigned to a donor chromosomal region, that haplotype can be used in that population or any subset thereof to determine whether an individual has a particular gene. See, for example, WO2003054229. Using automated high throughput marker detection platforms known to those of ordinary skill in the art makes this process highly efficient and effective.

Many of the PHM markers can readily be used as FLP markers to select for the gene loci on chromosomes 3 and/or 4, owing to the presence of insertions/deletion polymorphisms. Primers for the PHM markers can also be used to convert these markers to SNP or other structurally similar or functionally equivalent markers (SSRs, CAPs, indels, etc), in the same regions. One very productive approach for SNP conversion is described by Rafalski (2002a) Current opinion in plant biology 5 (2): 94-100 and also Rafalski (2002b) *Plant Science* 162: 329-333. Using PCR, the primers are used to amplify DNA segments from individuals (preferably inbred) that represent the diversity in the population of interest. The PCR products are sequenced directly in one or both directions. The resulting sequences are aligned and polymorphisms are identified. The polymorphisms are not limited to single nucleotide polymorphisms (SNPs), but also include indels, CAPS, SSRs, and VNTRs (variable number of tandem repeats). Specifically with respect to the fine map information described herein, one can readily use the information provided herein to obtain additional polymorphic SNPs (and other markers) within the region amplified by the primers listed in this disclosure. Markers within the described map region can be hybridized to BACs or other genomic libraries, or electronically aligned with genome sequences, to find new sequences in the same approximate location as the described markers.

In addition to SSR's, FLPs and SNPs, as described above, other types of molecular markers are also widely used, including but not limited to expressed sequence tags (ESTs), SSR markers derived from EST sequences, randomly amplified polymorphic DNA (RAPD), and other nucleic acid based markers.

Isozyme profiles and linked morphological characteristics can, in some cases, also be indirectly used as markers. Even though they do not directly detect DNA differences, they are often influenced by specific genetic differences. However, markers that detect DNA variation are far more numerous and polymorphic than isozyme or morphological markers (Tanksley (1983) *Plant Molecular Biology Reporter* 1:3-8).

Sequence alignments or contigs may also be used to find sequences upstream or downstream of the specific markers listed herein. These new sequences, close to the markers described herein, are then used to discover and develop functionally equivalent markers. For example, different physical and/or genetic maps are aligned to locate equivalent markers not described within this disclosure but that are within similar regions. These maps may be within the maize species, or even across other species that have been genetically or physically aligned with maize, such as rice, wheat, barley or sorghum.

In general, MAS uses polymorphic markers that have been identified as having a significant likelihood of co-segregation with *Fusarium* ear mold resistance. Such markers are presumed to map near a gene or genes that give the plant its *Fusarium* ear mold resistance phenotype, and are considered indicators for the desired trait, and hence, are termed QTL markers. Plants are tested for the presence of a favorable allele in the QTL marker, and plants containing a desired genotype at one or more loci are expected to transfer the desired genotype, along with a desired phenotype, to their progeny. The means to identify maize plants that have enhanced resistance to *Fusarium* ear mold by identifying plants that have a specified allele at any one of marker loci described herein, including the chromosome 3 marker loci, PHM12969, PHM1695, PHM12209, PHM2204, PHM9905, PHM13926, PHM10091, and PHM18211, and the chromosome 4 marker loci, PHM2015, PHM10326, PHM497, PHM4483, PHM5273, PHM939, PHM10892, PHM9363, PHM18162, PHM9942, PHM5247, PHM3985, PHM6226, and PHM10262, are presented herein.

Furthermore, favorable alleles (i.e., associated with enhanced *Fusarium* ear mold) identified herein include: a "C" at PHM12209.11, a "T" at PHM12209.20, a "C" at PHM12209.21, a "G" at PHM12209.22, a "C" at PHM12209.23, an "A" at PHM9905.11, a "T" at PHM9905.13, a "G" at PHM9905.35, a "T" at PHM2204.88, an "A" at PHM2204.105, a "C" at PHM13926.25, a "G" at PHM13926.27, a "G" at PHM13926.28, a "G" at PHM13926.32, a "C" at PHM10892.3, a "G" at PHM939.47, and an "A" at PHM939.48.

The QTL intervals presented herein find use in MAS to select plants that demonstrate enhanced resistance to *Fusarium* ear mold. Similarly, the QTL intervals can also be used to counter-select plants that have are more susceptible to *Fusarium* ear mold. Any marker that maps within the QTL interval (including the termini of the intervals) can be used for this purpose. The chromosome 3 interval is defined by and includes PHM12969 and PHM18211, while the chromosome 4 interval is defined by and includes PHM10892 and PHM10262. Plants with desirable marker alleles within the chromosome 3 and/or chromosome 4 intervals can be selected. QTL markers that have the strongest associations with *Fusarium* ear mold resistance are particularly useful for marker-assisted selection.

Haplotypes can also be used in MAS to introduce enhanced resistance to *Fusarium* ear mold into susceptible maize lines or varieties. A chromosome 3 haplotype associated with enhanced resistance to *Fusarium* ear mold can comprise at least one of the following: a "C" at PHM12209.11, a "T" at PHM12209.20, a "C" at PHM12209.21, a "G" at PHM12209.22, a "C" at PHM12209.23, an "A" at PHM9905.11, a "T" at PHM9905.13, a "G" at PHM9905.35, a "T" at PHM2204.88, an "A" at PHM2204.105, a "C" at PHM13926.25, a "G" at PHM13926.27, a "G" at PHM13926.28, and a "G" at PHM13926.32, or any other marker allele that is linked to and associated with any of the marker alleles identified herein as being associated with enhanced resistance to *Fusarium* ear mold. A chromosome 4 haplotype associated with enhanced resistance to *Fusarium* ear mold can comprise at least one of the following: a "C" at PHM10892.3, a "G" at PHM939.47, and an "A" at PHM939.48, or any other marker allele that is linked to and associated with any of the marker alleles identified herein as being associated with enhanced resistance to *Fusarium* ear mold.

Any allele that is in linkage disequilibrium with a haplotype comprising at least one of the following: a "C" at PHM12209.11, a "T" at PHM12209.20, a "C" at PHM12209.21, a "G" at PHM12209.22, a "C" at PHM12209.23, an "A" at PHM9905.11, a "T" at PHM9905.13, a "G" at PHM9905.35, a "T" at PHM2204.88, an "A" at PHM2204.105, a "C" at PHM13926.25, a "G" at PHM13926.27, a "G" at PHM13926.28, and a "G" at PHM13926.32, or a haplotype comprising at least one of the following: a "C" at PHM10892.3, a "G" at PHM939.47, and an "A" at PHM939.48 can also be used in MAS to select plants with enhanced resistance to *Fusarium* ear mold.

Maize Plants

The compositions and methods presented herein can be used to identify and/or select plants from the genus *Zea* (and more specifically, *Zea mays* L. ssp. Mays) that have enhanced resistance to *Fusarium* ear mold. The plants can be hybrids, inbreds, partial inbreds, or members of defined or undefined populations. They can be in any heterotic group, including, but not limited to, the stiff stalk and non stiff stalk groups.

Consequently, maize plants that are identified and/or selected by any of the methods presented herein are also a feature of the invention.

EXAMPLES

The following examples are offered to illustrate, but not to limit, the claimed invention. It is understood that the examples and embodiments described herein are for illustrative purposes only, and persons skilled in the art will recognize various reagents or parameters that can be altered without departing from the spirit of the invention or the scope of the appended claims.

Example 1

QTL Detection: Association Mapping Analysis

An association mapping strategy was undertaken to identify markers associated with *Fusarium* ear mold resistance in maize. In this association analysis, a collection of 475 maize lines was analyzed by DNA sequencing at 4000-10000 genes (genetic loci). The lines encompassed elite germplasm, commercially released cultivars, and other public varieties.

Phenotypic scores were obtained using the FUSERS scale provided in FIG. 5. An average score for each line was assigned based on data accumulated over multiple locations and multiple years.

A structure-based association analysis was conducted using standard association mapping methods, where the population structure is controlled using marker data. The model-based cluster analysis software, Structure, developed by Pritchard et al., (Genetics 155:945-959 (2000)) was used with haplotype data for 880 elite maize inbreds at two hundred markers to estimate admixture coefficients and assign the inbreds to seven subpopulations. This reduces the occurrence of false positives that can arise due to the effect of population structure on association mapping statistics. Kuiper's statistic for testing whether two distributions are the same was used to test a given marker for association between haplotype and phenotype in a given subpopulation (Press et al., Numerical Recipes in C, second edition, Cambridge University Press, NY (2002)).

A peak of significant marker-trait associations was identified on chromosome 3 (FIG. 3) in a stiff stalk group. TABLE 1 provides a listing of the maize markers significantly associated with the *Fusarium* ear mold resistance phenotype at the $p \leq 0.001$ level, representing an interval of ~4 cM on the internally derived genetic map. On the internally derived genetic map, this chromosomal interval is delineated by and includes markers PHM12969 at position 224.43 (p-value=$1.4 \times 10^{-4}$) and PHM1695 at position 228.76 (p-value=$1.28 \times 10^{-4}$). The most associated marker is PHM2204 at position 226.71 with a p-value of $2.05 \times 10^{-6}$. Positions are given in cM, with position zero being the first (most distal from the centromere) marker known at the beginning of the chromosome. The map positions in TABLE 1 are not absolute and represent an estimate of map position based on the internally derived genetic map (PHB).

TABLE 1

Chromosome 3 markers significantly associated with
Fusarium ear mold resistance at p ≤ 0.001 in
the stiff stalk subpopulation group

| Marker Name | Relative map position (cM) on PHB map | P-Value | Reference Sequence | Primer Sequences |
|---|---|---|---|---|
| PHM12969 | 224.43 | 1.40E−04 | SEQ ID NO: 1 | SEQ ID NOs: 23-26 |
| PHM2204 | 226.71 | 2.05E−06 | SEQ ID NO: 2 | SEQ ID NOs: 27-30 |
| PHM9905 | 226.83 | 1.47E−05 | SEQ ID NO: 3 | SEQ ID NOs: 31-34 |
| PHM12209 | 226.95 | 6.26E−05 | SEQ ID NO: 4 | SEQ ID NOs: 35-38 |
| PHM13926 | 227.97 | 4.94E−06 | SEQ ID NO: 5 | SEQ ID NOs: 39-42 |
| PHM10091 | 227.97 | 2.60E−04 | SEQ ID NO: 6 | SEQ ID NOs: 43-46 |
| PHM18211 | 228.29 | 8.20E−04 | SEQ ID NO: 7 | SEQ ID NOs: 47-50 |
| PHM1695 | 228.76 | 1.28E−04 | SEQ ID NO: 8 | SEQ ID NOs: 51-54 |

A peak of significant marker-trait associations was also identified on chromosome 4 (FIG. 4) in the same stiff stalk group. TABLE 2 provides a listing of the maize markers significantly associated with the Fusarium ear mold resistance phenotype at the p≤0.001 level, representing an interval of ~2 cM on the internally derived genetic map. On the internally derived genetic map, this chromosomal interval is delineated by and includes markers PHM939 at position 198.06 (p-value=7.00×10$^{-5}$) and PHM10262 at position 201.25 (p-value=1.38×10$^{-4}$). The most associated marker is PHM10892 at position 198.06 with a p-value of 4.44×10$^{-7}$. Positions are given in cM, with position zero being the first (most distal from the centromere) marker known at the beginning of the chromosome. The map positions in TABLE 2 are not absolute and represent an estimate of map position based on the internally derived genetic map (PHB).

TABLE 2

Chromosome 4 markers significantly associated with
Fusarium ear mold resistance at p ≤ 0.001 in
the stiff stalk subpopulation group

| Marker Name | Relative map position (cM) on PHB map | P-Value | Reference Sequence | Primer Sequences |
|---|---|---|---|---|
| PHM10892 | 198.06 | 4.44E−07 | SEQ ID NO: 10 | SEQ ID NOs: 59-62 |
| PHM939 | 198.06 | 7.00E−05 | SEQ ID NO: 9 | SEQ ID NOs: 55-58 |
| PHM5273 | 198.27 | 2.06E−04 | SEQ ID NO: 11 | SEQ ID NOs: 63-66 |
| PHM497 | 198.54 | 1.16E−04 | SEQ ID NO: 12 | SEQ ID NOs: 67-70 |
| PHM4483 | 199.67 | 1.00E−03 | SEQ ID NO: 13 | SEQ ID NOs: 71-74 |
| PHM2015 | 199.72 | 3.12E−04 | SEQ ID NO: 14 | SEQ ID NOs: 75-78 |
| PHM10326 | 199.78 | 8.80E−04 | SEQ ID NO: 15 | SEQ ID NOs: 79-82 |
| PHM9363 | 199.78 | 5.20E−04 | SEQ ID NO: 16 | SEQ ID NOs: 83-86 |
| PHM18162 | 200.62 | 9.20E−04 | SEQ ID NO: 17 | SEQ ID NOs: 87-90 |
| PHM9942 | 200.88 | 2.96E−04 | SEQ ID NO: 18 | SEQ ID NOs: 91-94 |
| PHM5247 | 200.93 | 2.40E−04 | SEQ ID NO: 19 | SEQ ID NOs: 95-98 |
| PHM3985 | 201.06 | 1.78E−04 | SEQ ID NO: 20 | SEQ ID NOs: 99-102 |
| PHM6226 | 201.25 | 9.20E−04 | SEQ ID NO: 21 | SEQ ID NOs: 103-106 |
| PHM10262 | 201.25 | 1.38E−04 | SEQ ID NO: 22 | SEQ ID NOs: 107-110 |

There were 145 lines assigned by the model-based cluster analysis software, Structure, to the stiff stalk subpopulation in which the QTLs for Fusarium ear mold resistance were detected.

Example 2

Physical Map Positions

The consensus sequences for each of the PHM markers were BLASTed to a database consisting of public corn sequenced BACs. TABLES 3 and 4 show the BACs for each marker that were identified as containing that marker, thereby delineating physical map regions where the QTLs are located.

TABLE 3

BAC hits for chromosome 3 PHM markers

| Marker Name | BAC hits |
|---|---|
| PHM12969 | c0437d18, c0094g18, b0219j14 |
| PHM1695 | c0467n10 |
| PHM12209 | c0467n10, b0184d17 |
| PHM2204 | c0289f16, b0184d17 |
| PHM9905 | c0289f16, b0184d17 |
| PHM13926 | b0444e07 |
| PHM10091 | c0146b03, b0444e07 |
| PHM18211 | c0482d19, c0060e22 |

TABLE 4

BAC hits for chromosome 4 PHM markers

| Marker Name | BAC hits |
|---|---|
| PHM10892 | b0269h08 |
| PHM939 | c0184j24 |
| PHM5273 | c0184j24 |
| PHM497 | c0516g10 |
| PHM4483 | c0239c09, c0215i19 |
| PHM2015 | b0185p07 |
| PHM10326 | b0194j21 |
| PHM9363 | b0408e05 |
| PHM18162 | c0067j19, b0408e05 |
| PHM9942 | c0197f23 |
| PHM5247 | c0510k02, c0112k06 |
| PHM3985 | c0483h18, b0200m05 |
| PHM6226 | c0237f22 |
| PHM10262 | c0237f22, c0069i21 |

Example 3

Haplotype Analysis for 113 Stiff Stalk Lines

In the association study in Example 2, the four most associated markers in the chromosome 3 region were PHM12209, PHM9905, PHM2204, and PHM13926. SNP polymorphisms that are associated with either a favorable or unfavorable *Fusarium* ear mold resistance phenotype can be identified, creating a haplotype that can be identified and selected for in plants. TABLE 5 shows the SNP polymorphisms at marker loci PHM12209, PHM9905, PHM2204, and PHM13926 that are associated with the favorable phenotype, or enhanced *Fusarium* ear mold resistance, and that can be used in haplotypic combinations to identify plants with enhanced *Fusarium* ear mold resistance.

TABLE 5

SNPs at Marker Loci PHM12209, PHM9905, PHM2204, and PHM13926

| Polymorphism | Position | High throughput SNP marker developed | Genotypes selected for favorable haplotype |
|---|---|---|---|
| PHM12209.11 | 208 | N/A | c |
| PHM12209.20 | 297 | PHM12209-20-U | t |
| PHM12209.21 | 328 | PHM12209-21-U | c |
| PHM12209.22 | 344 | N/A | g |
| PHM12209.23 | 365 | PHM12209-23-U | c |
| PHM9905.11 | 516 | N/A | a |
| PHM9905.13 | 531 | N/A | t |
| PHM9905.35 | 912 | N/A | g |
| PHM2204.88 | 750 | N/A | t |
| PHM2204.105 | 1166 | N/A | a |
| PHM13926.25 | 309 | N/A | c |
| PHM13926.27 | 315 | N/A | g |
| PHM13926.28 | 336 | N/A | g |
| PHM13926.32 | 360 | N/A | g |

In the association study in Example 2, the two most associated markers in the chromosome 4 region were PHM10892 and PHM939, and the SNP markers used for haplotyping are shown in TABLE 6. TABLE 6 shows the SNP polymorphisms at marker loci PHM10892 and PHM939 that are associated with the favorable phenotype, or enhanced *Fusarium* ear mold resistance, and that can be used in haplotypic combinations to identify plants with enhanced *Fusarium* ear mold resistance.

TABLE 6

SNPs at Marker Loci PHM10892 and PHM939 Useful for Identifying Genotypes Associated with Enhanced *Fusarium* Ear Mold Resistance

| Polymorphism | Position | High throughput SNP marker developed | Genotypes selected for favorable haplotype |
|---|---|---|---|
| PHM10892.3 | 646 | PHM10892-3-U | c |
| PHM939.47 | 373 | N/A | g |
| PHM939.48 | 389 | N/A | a |

PHM markers can be used to genotype the progeny via the sequencing of PCR products. SEQ ID NOs:23-110 represent the primers for each of the PHM marker loci listed in Tables 1 and 2. For PHM marker analysis, nested PCR reactions are performed, using the external and internal primers for each PHM marker. In the first PCR reaction, 0.90 μl of 10×PCR buffer, 0.18 μl of 10 mM dNTP mix, 0.27 μl of 50 mM MgCl$_2$, 1.50 μl of 2.5 μM external forward primer, 1.50 μl of 2.5 μM external reverse primer, 0.04 μl of Platinum Taq, 1.61 μl of ddH2O, and 3 μl of 1.5 ng/μl DNA are used. The thermocycling conditions constitute: 95° C. at 5 minutes; 94° C. for 20 seconds, 55° C. for 30 seconds, and 72° C. for 2 minutes, repeated for 24 cycles; 72° C. for 10 minutes; and a hold at 4° C. The DNA produced from the first round of PCR is then diluted 1:9 with TE for use in the second round of PCR. The reaction mix for the second round of PCR is the same except the internal sets of primers are used, and the DNA is the diluted DNA from the first round of PCR. The thermocycling conditions for the second round of PCR constitute: 95° C. at 5 minutes; 94° C. for 20 seconds, 55° C. for 30 seconds, and 72° C. for 2 minutes, repeated for 28 cycles; 72° C. for 10 minutes; and a hold at 4° C. The PCR products are then sequenced directly.

In addition, high throughput markers can be developed for useful polymorphisms. These markers will distinguish the parents from one another, preferably using a high throughput assay, and are used to genotype the segregating progeny plants. Production markers were developed, for example, from SNPs PHM12209.20, PHM12209-21, PHM12209-23, and PHM10892-3. These particular markers were designed for use with the Invader Plus high-throughput platform. The primer and probe sequences for these markers are shown in TABLE 7 and represent SEQ ID NOs:111-126.

TABLE 7

Marker information for high-throughput SNP markers

| Marker Name | Primer 1 | Primer 2 | Allele 1 | Allele 2 | Probe 1 | Probe 2 |
|---|---|---|---|---|---|---|
| PHM12209-20-U | SEQ ID NO: 111 | SEQ ID NO: 112 | C | T | SEQ ID NO: 113 | SEQ ID NO: 114 |
| PHM12209-21-U | SEQ ID NO: 115 | SEQ ID NO: 116 | T | C | SEQ ID NO: 117 | SEQ ID NO: 118 |
| PHM12209-23-U | SEQ ID NO: 119 | SEQ ID NO: 120 | T | C | SEQ ID NO: 121 | SEQ ID NO: 122 |
| PHM10892-3-U | SEQ ID NO: 123 | SEQ ID NO: 124 | C | T | SEQ ID NO: 125 | SEQ ID NO: 126 |

Out of 124 lines in the Stiff Stalk subpopulation, 113 had sufficient genotypic and phenotypic data to be analyzed further.

For the chromosome 3 QTL, forty seven lines had the favorable haplotype (i.e. all of the SNPs identified in Table 5) and an average FUSERS score of 5.1 (standard error=0.1), while sixty six lines had other haplotypes and an average score of 4.3 (standard error=0.2).

For the chromosome 4 QTL, twenty two lines had the favorable haplotype (i.e. all of the SNPs identified in Table 6) and an average FUSERS score of 5.5 (standard error=0.2). Ninety one lines had other haplotypes and an average FUSERS score of 4.4 (standard error=0.1).

Example 4

Validation within a Group of Stiff-Stalk Inbreds

A collection of 54 inbreds, differing in their haplotypes at the chromosome 3 (c3) and chromosome 4 (c4) marker-trait loci were evaluated for *Fusarium* ear mold resistance in 2006 in Kauai, Hi., where natural infection occurs. For each marker-trait locus, the inbreds were classified as having either a favorable or unfavorable haplotype based on actual genotyping of the entry or the direct progenitor inbreds. For the c3 marker-trait association, a favorable haplotype comprised an 'A' at PHM2204-97, while an unfavorable haplotype comprised a 'G' at the same locus.

For the c4 marker-trait association, a favorable haplotype comprised a 'C' at PHM10892-3, while an unfavorable haplotype comprised a 'T' at the same locus.

Inbreds were evaluated for ear mold reaction according to the FUSERS scoring scale shown on FIG. 5. There were three replicates in the experiment. Data were analyzed and least squares (LS) means were obtained using procGLM (SAS statistical package).

The mean ear mold score of inbreds carrying a favorable haplotype at the c3 locus did not differ significantly from the mean ear mold score of inbreds carrying an unfavorable haplotype. However inbreds carrying a favorable haplotype at the c4 locus scored, on average, significantly higher than inbreds carrying an unfavorable haplotype at the same locus. FUSERS LS means scores for each locus haplotype are shown on TABLE 8.

TABLE 8

FUSERS Least Squares Means Obtained in Kauai, HI in 2006

| c3 | | c4 | |
|---|---|---|---|
| Unfavorable | Favorable$^a$ | Unfavorable | Favorable$^a$ |
| 5.7 ± 0.2 | 5.9 ± 0.2$^{ns}$ | 5.3 ± 0.1 | 6.3 ± 0.2*** |

$^a$probability for the comparison of haplotypes within a marker trait locus
$^{ns}$not significant,
***significant at p < 0.001

Example 5

Validation within a Second Group of Stiff-Stalk Inbreds

A collection of stiff-stalk inbreds, with differing haplotypes at the c3 and c4 marker-trait association loci, were evaluated for *Fusarium* ear mold resistance in 2007 at two US locations (Cairo, Ga., and Woodland, Calif.) where natural infection occurs. For each marker-trait locus, the inbreds were classified as having either a favorable or unfavorable haplotype based on actual genotyping of the entry or the direct progenitor inbreds. For the c3 marker-trait association, a favorable haplotype comprised an 'A' at PHM2204-97 while an unfavorable haplotype comprised a 'G' at the same locus. For the c4 marker-trait association, a favorable haplotype comprised a 'C' at PHM10892-3 while an unfavorable haplotype comprised a 'T' at the same locus.

A phenotypic score for each entry was obtained by scoring all individual ears within a row using the FUSERS scale provided in FIG. 5 and calculating a total row score with the following formula:

FUSINDEX=[(1×number of ears with unfavorable phenotype)+(5×number of intermediate ears)+ (9×number of ears with favorable phenotype)]/ total number of ears In 2007, disease pressure was light at the Cairo location and sufficient for effective scoring at the Woodland site. Phenotypic scores were obtained for 43 inbreds at Cairo and 45 inbreds at Woodland, with 32 of these inbreds being evaluated at both locations. There were three replicates in Cairo and six in Woodland. The statistical package ASRemI was used to analyze data and obtained predicted mean FUSERS scores.

Across locations, the average FUSINDEX score of inbreds having the favorable haplotype at c3 was significantly higher than the average FUSINDEX score of inbreds carrying the unfavorable haplotype. This difference in average scores was also highly significant at the individual Woodland location.

Across locations, the average FUSINDEX score of inbreds having the favorable haplotype at c4 was significantly higher than the average FUSINDEX score of inbreds carrying the unfavorable haplotype. This difference in average scores was also significant at the Cairo location and highly significant at the Woodland location.

The interaction effect of both loci was not significant, indicating the loci displayed additive effects on the phenotype. Predicted mean FUSINDEX scores for each haplotype class at each marker locus association are shown in TABLE 9. Predicted mean FUSINDEX scores for each c3/c4 combined haplotype class are shown in TABLE 10.

TABLE 9

Predicted Mean FUSINDEX Scores Obtained in 2007 for the Haplotype Classes at each Marker-Trait Locus

| | c3 | | c4 | |
|---|---|---|---|---|
| Location | Unfavorable | Favorable$^a$ | Unfavorable | Favorable$^a$ |
| Cairo, GA | 6.7 ± 0.2 | 6.9 ± 0.2$^{ns}$ | 6.4 ± 0.2 | 7.2 ± 0.3* |
| Woodland, CA | 4.7 ± 0.2 | 5.4 ± 0.2*** | 4.6 ± 0.2 | 5.5 ± 0.2*** |
| Across both | 5.6 ± 0.2 | 6.1 ± 0.2*** | 5.4 ± 0.2 | 6.3 ± 0.2* |

$^a$probability for the comparison of haplotypes within a marker trait locus
$^{ns}$not significant,
*significant at p < 0.05,
***significant at p < 0.001

TABLE 10

Predicted Mean FUSINDEX Scores Obtained in 2007 for the Four Combined Haplotype Classes.

| | c3/c4 combined haplotypes | | | |
|---|---|---|---|---|
| Location | Unfavorable/ Unfavorable | Unfavorable/ Favorable | Favorable/ Unfavorable | Favorable/ Favorable |
| Cairo, GA | 6.3 ± 0.2 | 7.1 ± 0.3 | 6.5 ± 0.2 | 7.3 ± 0.3 |
| Woodland, CA | 4.2 ± 0.2 | 5.2 ± 0.3 | 4.9 ± 0.2 | 5.9 ± 0.2 |
| Across both | 5.1 ± 0.2 | 6.0 ± 0.2 | 5.6 ± 0.2 | 6.5 ± 0.2 |

What is claimed is:

1. A method of identifying a maize plant with enhanced resistance to *Fusarium* ear mold, the method comprising:
   a. isolating nucleic acids from a maize plant;
   b. analyzing the isolated nucleic acids for the presence of a haplotype associated with the enhanced resistance to *Fusarium* ear mold, wherein said haplotype is located within a chromosomal interval comprising and flanked by PHM12969 and PHM18211 and comprises:
      i. a "C" at PHM12209.11,
      ii. a "T" at PHM12209.20,
      iii. a "C" at PHM12209.21,
      iv. a "G" at PHM12209.22,
      v. a "C" at PHM12209.23,
      vi. an "A" at PHM9905.11,
      vii. a "T" at PHM9905.13,
      viii. a "G" at PHM9905.35,
      ix. a "T" at PHM2204.88,
      x. an "A" at PHM2204.105,
      xi. a "C" at PHM13926.25,
      xii. a "G" at PHM13926.27,
      xiii. a "G" at PHM13926.28, and
      xiv. a "G" at PHM13926.32; and
   c. selecting the maize plant if the haplotype is detected.

2. A method of selecting a maize plant with enhanced resistance to *Fusarium* ear mold, the method comprising:
   a. identifying a first maize plant that has a haplotype within a chromosomal interval comprising and flanked by PHM12969 and PHM18211, said haplotype comprising:
      i. a "C" at PHM12209.11,
      ii. a "T" at PHM12209.20,
      iii. a "C" at PHM12209.21,
      iv. a "G" at PHM12209.22,
      v. a "C" at PHM12209.23,
      vi. an "A" at PHM9905.11,
      vii. a "T" at PHM9905.13,
      viii. a "G" at PHM9905.35,
      ix. a "T" at PHM2204.88,
      x. an "A" at PHM2204.105,
      xi. a "C" at PHM13926.25,
      xii. a "G" at PHM13926.27,
      xiii. a "G" at PHM13926.28, and
      xiv. a "G" at PHM13926.32;
   b. crossing said first maize plant to a second maize plant;
   c. evaluating progeny plants for the haplotype of the first maize plant; and
   d. selecting the progeny plants that possess the at haplotype of the first maize plant.

* * * * *